(12) United States Patent
Roy

(10) Patent No.: US 10,688,176 B2
(45) Date of Patent: Jun. 23, 2020

(54) REOVIRIDAE VACCINE

(71) Applicant: London School of Hygiene & Tropical Medicine, London (GB)

(72) Inventor: Polly Roy, London (GB)

(73) Assignee: London School of Hygiene & Tropical Medicine, London (GB)

( * ) Notice: Subject to any disclaimer, the term of this patent is extended or adjusted under 35 U.S.C. 154(b) by 0 days.

(21) Appl. No.: 16/093,503

(22) PCT Filed: Apr. 10, 2017

(86) PCT No.: PCT/GB2017/050994
§ 371 (c)(1),
(2) Date: Oct. 12, 2018

(87) PCT Pub. No.: WO2017/187131
PCT Pub. Date: Nov. 2, 2017

(65) Prior Publication Data
US 2019/0060442 A1     Feb. 28, 2019

(30) Foreign Application Priority Data
Apr. 26, 2016  (GB) .................................. 1607196.1

(51) Int. Cl.
| | |
|---|---|
| *A61K 39/15* | (2006.01) |
| *A61K 39/12* | (2006.01) |
| *C12N 7/00* | (2006.01) |
| *A61K 31/7105* | (2006.01) |
| *A61K 45/06* | (2006.01) |
| *A61K 39/00* | (2006.01) |

(52) U.S. Cl.
CPC .......... *A61K 39/15* (2013.01); *A61K 31/7105* (2013.01); *A61K 39/12* (2013.01); *A61K 45/06* (2013.01); *C12N 7/00* (2013.01); *A61K 2039/5254* (2013.01); *A61K 2039/552* (2013.01); *A61K 2039/70* (2013.01); *C12N 2720/12121* (2013.01); *C12N 2720/12134* (2013.01); *C12N 2720/12152* (2013.01); *C12N 2720/12162* (2013.01)

(58) Field of Classification Search
CPC ........ C12N 15/86; C12N 15/70; C12N 15/74; C12N 2720/12162; C12N 2760/12221; C12N 2760/12262; C12N 2800/22; C12N 2800/24
See application file for complete search history.

(56) References Cited

U.S. PATENT DOCUMENTS

| | | | |
|---|---|---|---|
| 8,673,315 | B2 | 3/2014 | Roy et al. |
| 9,457,076 | B2 * | 10/2016 | Roy ........................ A61K 39/15 |
| 2013/0337010 | A1 | 12/2013 | Palmarini et al. |

FOREIGN PATENT DOCUMENTS

| | | |
|---|---|---|
| AU | 2014201189 A1 | 3/2014 |
| WO | WO 2009/068870 A1 | 6/2009 |
| WO | WO 2016/071850 A1 | 5/2016 |

OTHER PUBLICATIONS

Matsuo et al., "A reverse genetics system of African horse sickness virus reveals existence of primary replication," *FEBS Letters* 584: 3386-3391 (2010).
Matsuo et al., "Generation of Replication-Defective Virus-Based Vaccines That Confer Full Protection in Sheep against Virulent Bluetongue Virus Challenge," *Journal of Virology* 85(19): 10213-10221 (2011).
Search Report issued in Great Britain Application No. 1607196.1, dated Jan. 24, 2017 (4 pages).
Kaname et al., "Recovery of African horse sickness virus from synthetic RNA," *J Gen Virol*. 94:2259-2265, 2013.
Kar and Roy, "Defining the structure-function relationships of bluetongue virus helicase protein VP6," *J Virol*. 77:11347-11356, 2003.
Lulla et al., "Assembly of Replication-Incompetent African Horse Sickness Virus Particles: Rational Design of Vaccines for All Serotypes," *J Virol*. 90:7405-7414, 2016.
Matsuo and Roy, "Bluetongue virus VP6 acts early in the replication cycle and can form the basis of chimeric virus formation," *J Virol*. 83:8842-8848, 2009.
Ratinier et al., "Identification and characterization of a novel non-structural protein of bluetongue virus," *PLoS Pathog*. 7:e1002477, 2011.
Yi et al., "Sequences within the VP6 molecule of bluetongue virus that determine cytoplasmic and nuclear targeting of the protein," *J Virol* 70:4778-4782, 1996.
Zwart et al., "Characterising Non-Structural Protein NS4 of African Horse Sickness Virus," *PLoS One* 10:e0124281, 2015.
PCT/GB2017/050994 International Search Report and Written Opinion dated Jun. 7, 2017 (8 pages).

* cited by examiner

*Primary Examiner* — Bao Q Li
(74) *Attorney, Agent, or Firm* — Klarquist Sparkman, LLP

(57) ABSTRACT

The invention relates to an isolated African horse sickness virus (AHSV) ssRNA comprising a plurality of mutations; a complementary cell for replication of a vaccinal viral strain from said ssRNA; a vaccinal viral strain derived from said ssRNA; use of said vaccinal viral strain and/or isolated ssRNA in the vaccination of an animal against an infection by AHSV; a method of vaccination comprising same; and a pharmaceutical composition comprising said vaccinal viral strain and/or said isolated ssRNA.

23 Claims, 16 Drawing Sheets

Specification includes a Sequence Listing.

Figure 1

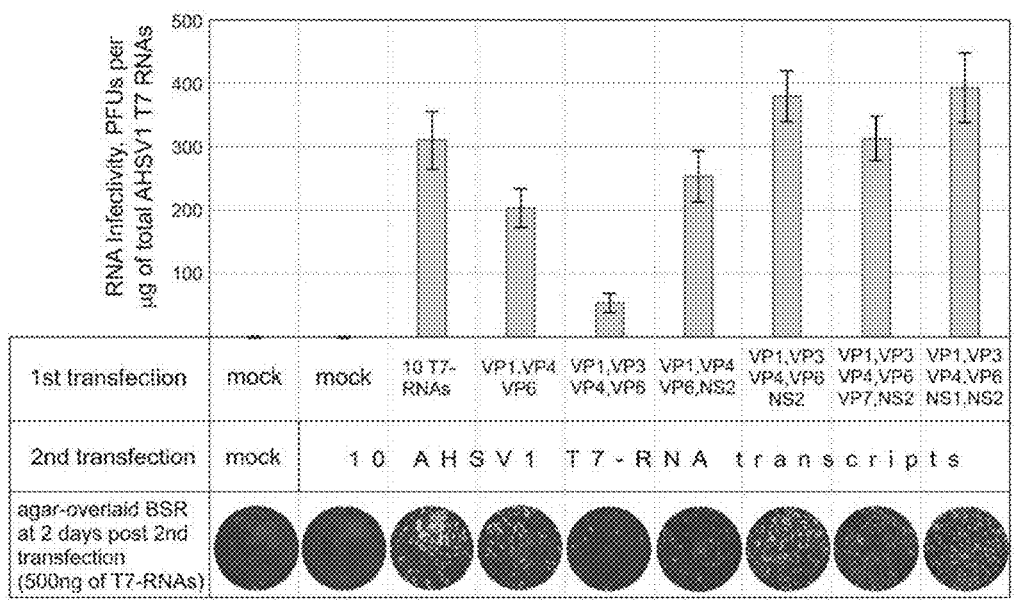

Figure 3A passage number of BSR-VP6
BSR 1  5  10  15  20  25  30
VP6

Figure 3C mock   rec-AHSV1   def-AHSV1 virus rescue on BSR-VP6, 56 h post 2nd transfection

Figure 3B

AHSV1 primary replication complex
VP3, VP1, VP4, VP6, NS2
+ 10 AHSV1 T7-RNAs
(S9multistop (rec VP6/NS4 produced))

BSR-VP6 cell line
VP6 defective AHSV1 particles
- VP2, VP5 } outer shell
- VP7 middle shell
- VP3 inner shell
- ds-S9multistop
- VP1, VP4, VP6 } replicase

Growth on complementary cell line (BSR-VP6)

| | Final titer, PFU/ml |
|---|---|
| def-AHSV1 | $2 \times 10^7$ |
| def-AHSV2 | $1 \times 10^7$ |
| def-AHSV3 | $7 \times 10^7$ |
| def-AHSV4 | $9 \times 10^7$ |
| def-AHSV5 | $2 \times 10^7$ |
| def-AHSV6 | $2 \times 10^7$ |
| def-AHSV7 | $2 \times 10^7$ |
| def-AHSV8 | $1 \times 10^8$ |
| def-AHSV9 | $7 \times 10^7$ |
| recAHSV1 | $2 \times 10^7$ |

Figure 5B — BSR cells

Figure 5C — Insect KC cells

Figure 5D — Equine E. Derm cells

Mice survival after challenge infection

| | |
|---|---|
| —— | control |
| —·—·— | AHSV1$_{inf}$ |
| — — — | def-AHSV1$_{vac}$ AHSV1$_{inf}$ |
| —··—··— | AHSV4$_{inf}$ |
| —·· ·· — | def-AHSV4$_{vac}$ AHSV4$_{inf}$ |

Figure 6A

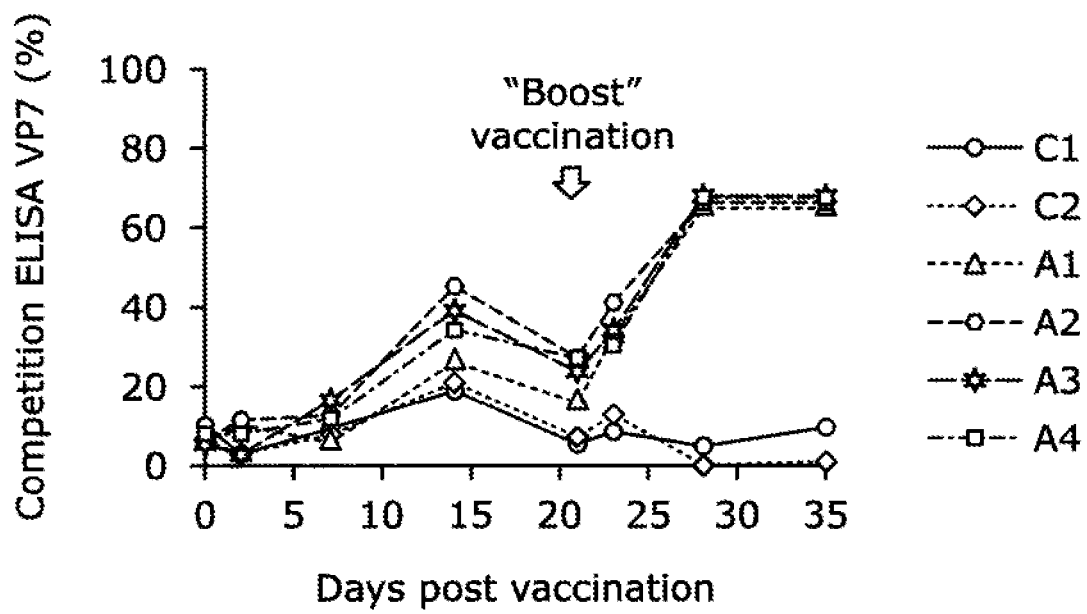
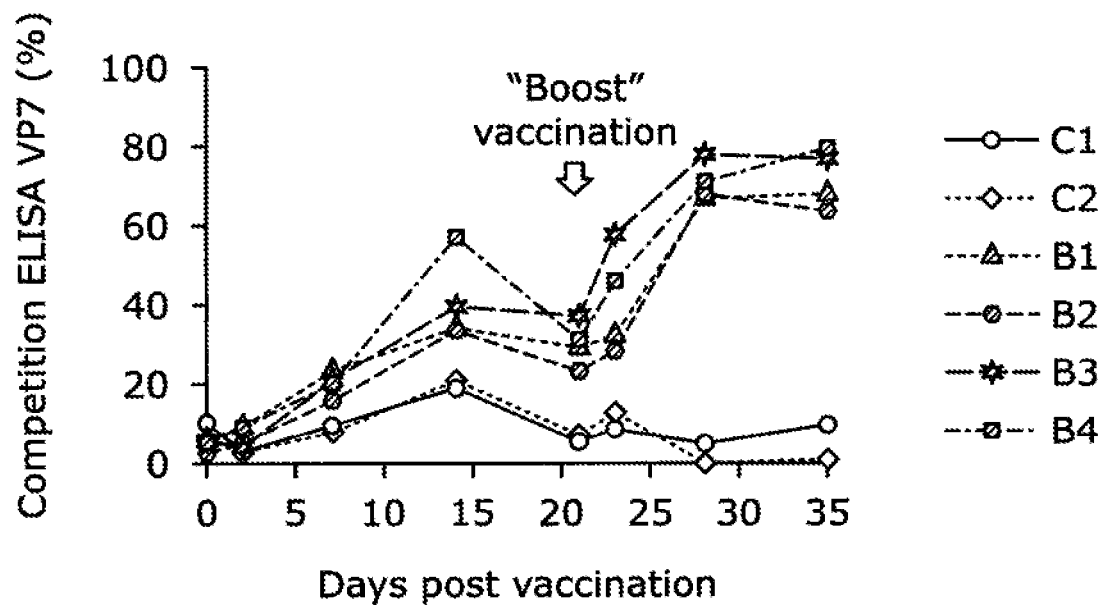
Figure 8

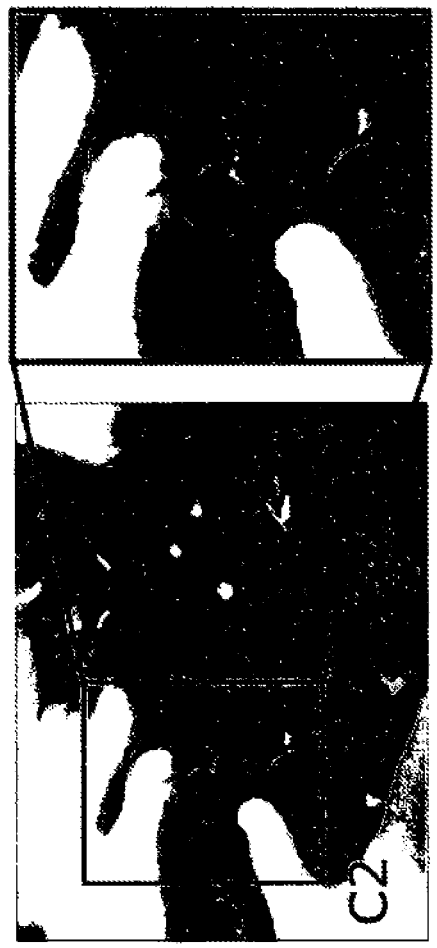
Figure 9B

Figure 11A

```
                910        920        930        940        950        960        970        980        990       1000
              ....|....|....|....|....|....|....|....|....|....|....|....|....|....|....|....|....|....|....|....|
AHSV1_s9      AGGATGAAATCAAAGTGTTCAAACTCAAAGCTCTTCTATCAGGTATATTAGTAATAGAATGGAAGATGTTTTAAGGGCGAAGGCGATGTTCACAGCGCC
multistopS9   ....................................................................................................

1010       1020       1030       1040       1050       1060       1070       1080       1090       1100
              ....|....|....|....|....|....|....|....|....|....|....|....|....|....|....|....|....|....|....|....|
AHSV1_s9      GACAGGTGATGAGGGGTGGAAGGAGGTTGCTAAAGCAGCAGCGACTCAGCGTACCAACATCATGGCGTATGTGCAGCGAAGGGAAGGCGATGGATTGAAAGAG
multistopS9   .....................................................................................................

1110       1120       1130       1140       1150       1160       1170
              ....|....|....|....|....|....|....|....|....|....|....|....|....|....|.
AHSV1_s9      CTTTTACATTTGATTGATCATATCTAGGTCCAGGGGTAAACGGCAGCTTGAGGGCAACTTAAAAACTTAC
multistopS9   .....................................................................
```

Figure 11B

SEQUENCE LISTING

<160> NUMBER OF SEQ ID NOS: 1

<210> SEQ ID NO 1
<211> LENGTH: 1169
<212> TYPE: DNA
<213> ORGANISM: African horse sickness virus

<400> SEQUENCE: 1

```
gttaaataag ttgtctcatg tcttcggcat tactcctcgc acctggcgat ctaatcgaaa      60
aagcaaagcg cgagctcgag cagcgctcga taactccgct cttgcgggag aaaaaatcga     120
aagaagccaa atctaaatta aaagaagatg gggagaagaa gaacaagagt gaagaggaaa     180
agaacaaaat acgtgatgat cgaagagtgg agagccagaa atctgaggga ggcggatcag     240
```

```
ccgattgtca acgcggcgca ggaagcgcag gagcaaattg cgcaacataa acataaggat    300
aagtggaagt gcaggagcaa ggaccggggt tgaagaggga ggagtgggag aagcggattc    360
gagatctgga ggacattgat aataaggtgc agcctcggat ggaaagggag tgggtaaatc    420
taagaccgga gtagatcgtg tcgctaatga tgatgcaaca cgcaatgttg gttccagtga    480
ggtatcatct ggtggaatca cttcaggagg tcttcaaggc cgaggaggac tcgttgcaaa    540
gagtagtgaa tgtggcgggg aaccattgga taggacaggc ggccgcagct gaaattgata    600
aacttgagga gaggaggcaa aggctggagg gggcgataga cggattggag gattagctac    660
gcaggagatt gccgactttg tgaagaagaa gatcggagtt gaagttcagg tcttttccaa    720
aggaatgacc aacttattta ctgtagataa atcattgctt gagcgggatg ggttagggag    780
ggaggacatt ctacatcaat cagatattgt aaaagagatt agagtaagtg ataaaaaagt    840
caagattatt cctctttcta cagtgaagag ataataagcg gaattcggag gaacagagga    900
ggatgaaatc aaagttgttc aaactcaaag ctcttctatc aggtatatta gtaatagaat    960
ggaagatgtt ttaagggcga aggcgatgtt cacagcgccg acaggtgatg aggggtggaa   1020
ggaggttgct aaagcagcga ctcagcgtcc taacatcatg gcgtatgtgc acgaagggga   1080
aggcgatgga ttgaaagagc ttttacattt gattgatcat atctaggtcc aggggtaaac   1140
ggcagcttga gggcaactta aaaacttac                                      1169
```

REOVIRIDAE VACCINE

CROSS REFERENCE TO RELATED APPLICATIONS

This is the U.S. National Stage of International Application No. PCT/GB2017/050994, filed Apr. 10, 2017, which was published in English under PCT Article 21(2), which in turn claims the benefit of GB Application No. 1607196.1, filed Apr. 26, 2016.

FIELD OF THE INVENTION

The invention relates to an isolated African horse sickness virus (AHSV) ssRNA comprising a plurality of mutations; a complementary cell for replication of a vaccinal viral strain from said ssRNA; a vaccinal viral strain derived from said ssRNA; use of said vaccinal viral strain and/or isolated ssRNA in the vaccination of an animal against an infection by AHSV; a method of vaccination comprising same; and a pharmaceutical composition comprising said vaccinal viral strain and/or said isolated ssRNA.

BACKGROUND OF INVENTION

Among closely related orbiviruses (Reoviridae family), such as Bluetongue virus (BTV), Epizootic haemorrhagic disease virus (EHDV) and African horse sickness virus (AHSV), the latter is known to cause the most severe morbidity and mortality in infected animals. In susceptible horses, the AHSV can cause different forms of disease ranging from mild fever to an acute fever where mortality reaches 95-100%. Although AHSV is endemic to sub-Saharan Africa, occasional outbreaks have been reported in North Africa, Pakistan, India, Spain and Portugal, and these outbreaks have had significant social and economic impact. The afore three orbiviruses are transmitted by midges of the genus *Culicoides* that are also found throughout Europe and the USA, thus increasing the potential geographic risk of AHSV outbreak, as, indeed, has been reported for BTV and EHDV.

The genome sequence of AHSV is divergent from BTV and EHDV. Only nine serotypes of the AHSV virus, AHSV1-AHSV9, have been identified. Vaccination with a live-attenuated polyvalent AHSV vaccine (LAV) is currently used to control the disease in Africa. However, this vaccine is considered unsafe due to adverse side effects; it causes viremia and it also has the potential to re-assort with field isolates thus risking the introduction of new virus serotypes into naïve geographical locations.

Therefore, there is a need for a rationally designed safe AHSV vaccine. Challengingly, the likely obstacles in the development of a safe vaccine are fundamental to its characteristics, besides the need for safe and efficient vaccine preparation the vaccine must be: (i) technically simple and reproducible, this is crucial for upscaling of production; (ii) cost-effective, which is directly dependent on: the number of virus like particles (VLPs) produced per cell, the heterologous nature of the vaccines, as well as the easiness of downstream processing. Unfortunately, subunit vaccines based on purified proteins, generally do not provide sufficient and long-lasting protection, moreover, they are costly to produce.

AHSV is a non-enveloped virus containing 10 double-stranded RNA (dsRNA) segments (S1-S10). The outer capsid is composed of two major structural proteins VP2 and VP5. The serotype-determining VP2 is the most variable viral protein, being the major target of a protective immune response. The core particle consists of two concentric layers: the surface VP7 layer and the inner VP3 layer, which enclose the 10 dsRNAs and a complex of replication enzymes VP1, VP4 and VP6. Comparisons between the sequences of the capsid proteins VP2, VP3, VP5 and VP7 of BTV10 with those of EHDV1 and AHSV4 have revealed the close relationship between these viruses: the inner core proteins, VP3 and VP7, are the most conserved, whereas outermost proteins, VP2 and VP5, are the most variable. Whilst previous structural studies of BTV have revealed details of BTV particle organization, currently, only the structure of a (top) domain of VP7 has been reported for AHSV, therefore analysis of AHSV virus functioning and any subsequent rational structure-based vaccine design is not possible for AHSV.

In the past decade, reverse genetics (RG) technology has revolutionized the understanding of viral replication and pathogenesis, and made a great contribution towards the development of vaccine technologies. However, whilst the RG technology for wildtype AHSV strains has been developed, it needs significant improvement to increase the efficiency of rescued virus production.

Herein we disclose the creation of mutated, replication-competent, propagation-disabled virus particles. Notably, passaging in a complementary cell line did not reveal changes in the mutated segment, which would restore any mutated ORFs. Further, replication efficiencies were close to wild-type (wt) AHSV thus generating substantial protein levels for vaccine development. This therefore represents a stable, superior and efficient vaccine therapy.

As a proof of principle, vaccination of IFNAR−/− mice with said vaccine and challenged with two virulent strains of AHSV showed efficient protection against homologous infection. Moreover, vaccination of AHSV natural hosts, e.g. ponies with a monoserotype (ECRA.A4) vaccine and one multivalent cocktail (ECRA.A1/4/6/8) vaccine showed protection against a virulent AHSV4. Furthermore, the multivalent cocktail vaccinated ponies produced neutralizing antibodies against all the serotypes present in the cocktail, and a foal born during the trial was healthy and had no viremia. These results validate the suitability of the technology as vaccines for AHSV.

STATEMENTS OF INVENTION

According to a first aspect of the invention there is therefore provided an isolated viral ssRNA derived from the genome of a African horse sickness virus (AHSV virus) wherein the ssRNA comprises at least a part of S9 segment of said virus and having therein a plurality of mutations in S9 segment of said virus wherein each mutation, at least after being introduced into said ssRNA, provides or encodes a stop codon.

Many viruses have a number of different serotypes. For example, AHSV has 9 different serotypes. Different serotypes can have slightly different surface proteins and may even differ in the number of genes contained in their respective genomes. Further, in the future, as yet undiscovered serotypes are likely to develop. Therefore, the present invention is intended to encompass any possible serotype of AHSV. Additionally, the present invention is intended to encompass any possible combination of AHSV serotypes.

As will be appreciated by those skilled in the art, reference herein to a stop codon refers to a nucleotide triplet within messenger RNA that signals a termination of translation of the protein encoded by the amino acid sequence of said RNA. This can include, but is not limited to, the known stop codons of RNA namely UAG, UAA or UGA. Therefore, production of any one such stop codons in the ssRNA of S9 segment leads to termination of translation and thus production of the protein encoded by same. Alternatively, as also known to those skilled in the art, a stop codon can be introduced as a consequence of a frameshift mutation wherein introduction/deletion of one or two nucleotides causes a shift in the reading frame of the ssRNA such that a stop codon then results.

In yet a further preferred embodiment, said mutations destroy the function of at least one essential gene.

Reference herein to the term "essential gene" refers to a gene which is essential for the virus to be pathogenic, and as such when the function of the essential gene is destroyed, the resulting vaccinal viral strain is non-pathogenic. This is a necessary requirement in vaccine generation. The mutations can be in any essential gene which, after introduction of said mutations, results in the virus being converted into a non-pathogenic phenotype.

Preferably, the mutations are introduced in an enzymatic protein, for example, in the viral polymerase, helicase or capping enzymes. Alternatively, any non-structural proteins can be inactivated. In this case, the essential gene is preferably one encoded by the S9 segment, such as but not limited to, VP6 and NS4.

In a further preferred embodiment, the mutations are such that the function of more than one essential gene is destroyed. This helps to ensure that the virus does not revert back to a pathogenic phenotype. Most preferably said mutations destroy the function of at least VP6 and NS4.

In yet a further preferred embodiment, said mutations are introduced at or between nucleotides 288-877 of S9 segment. Preferably said mutations are introduced at or between one or more of the following nucleotide sites selected from the group comprising or consisting of: 288-304; 377-386; 590-608; and 872-877. More ideally, at least one mutation is introduced into each of said nucleotide sites, ideally, a plurality of mutations are introduced into each of said nucleotide sites. More ideally still, at least the following mutations are introduced in said nucleotide sites:

a. at least 3 mutations at or between site 288-304;
 b. at least 3 mutations at or between site 377-386;
 c. at least 3 mutations at or between site 590-608; and
 d. at least 2 mutations at or between site 872-877.

Most ideally, additionally or alternatively, a frame-shift mutation is introduced at or between site 288-304 that destroys the function of NS4.

As shown in FIG. 11 we have used the following substitutions:

C to A at 289;
G to T at 294;
G to A at 295;
G to T at 300;
G to A at 301;
G to T at 378;
G to T at 381;
G to A at 382;
C to T at 384;
G to A at 386;
G to T at 591;
C to G at 598;
A to T at 600;
G to T at 606;
A to G at 607;
G to A at 608;
A to T at 873;
T to A at 874;
G to A at 875;
A to T at 876; and
T to A at 877.

Accordingly, in a preferred embodiment the invention concerns the use of any one or more, including all and any combination, of the afore multiple stop mutations giving rise to multiple stop codons. Although those of skill in the art will appreciate that other substitutions, having the same technical effect, can also be used to work the invention.

We therefore have introduced or provided a number (typically 11) of stop codons (typically TAA or TGA) throughout the S9 gene disrupting the ORFs of VP6 and NS4, but retaining the length of the obtained S9 multistop, thus minimizing the genetic pressure on the defective AHSV, ideally strain AHSV1, rescue and replication. Whilst the invention is practised herein using 11 stop codons those skilled in the art will appreciate more or less can be used and that the stop codons can be of any type, although we have ideally used TAA and TGA.

Indeed, it is most preferred aspect the invention comprises a ssRNA having SEQ ID No: 1 or a sequence that has, in ascending order of preference, at least 75%, 80%, 85%, 90%, 95%, 96%, 97%, 98%, 99% identity therewith.

```
SEQ ID No: 1 S9multistop:
GTTAAATAAGTTGTCTCATGTCTTCGGCATTACTCCTCGCACCTGGCGAT

CTAATCGAAAAAGCAAAGCGCGAGCTCGAGCAGCGCTCGATAACTCCGCT

CTTGCGGGAGAAAAAATCGAAAGAAGCCAAATCTAAATTAAAAGAAGATG

GGGAGAAGAAGAACAAGAGTGAAGAGGAAAAGAACAAAATACGTGATGAT

CGAAGAGTGGAGAGCCAGAAATCTGAGGGAGGCGGATCAGCCGATTGTCA

ACGCGGCGCAGGAAGCGCAGGAGCAAATTGCGCAACATAAACATAAGGAT

AAGTGGAAGTGCAGGAGCAAGGACCGGGGTTGAAGAGGGAGGAGTGGGAG

AAGCGGATTCGAGATCTGGAGGACATTGATAATAAGGTGCAGCCTCGGAT

GGAAAGGGAGTGGGTAAATCTAAGACCGGAGTAGATCGTGTCGCTAATGA

TGATGCAACACGCAATGTTGGTTCCAGTGAGGTATCATCTGGTGGAATCA

CTTCAGGAGGTCTTCAAGGCCGAGGAGGACTCGTTGCAAAGAGTAGTGAA

TGTGGCGGGGAACCATTGGATAGGACAGGCGGCCGCAGCTGAAATTGATA

AACTTGAGGAGAGGAGGCAAAGGCTGGAGGGGGCGATAGACGGATTGGAG

GATTAGCTACGCAGGAGATTGCCGACTTTGTGAAGAAGAAGATCGGAGTT

GAAGTTCAGGTCTTTTCCAAAGGAATGACCAACTTATTTACTGTAGATAA

ATCATTGCTTGAGCGGGATGGGTTAGGGAGGGAGGACATTCTACATCAAT

CAGATATTGTAAAAGAGATTAGAGTAAGTGATAAAAAAGTCAAGATTATT

CCTCTTTCTACAGTGAAGAGATAATAAGCGGAATTCGGAGGAACAGAGGA

GGATGAAATCAAAGTTGTTCAAACTCAAAGCTCTTCTATCAGGTATATTA

GTAATAGAATGGAAGATGTTTTAAGGGCGAAGGCGATGTTCACAGCGCCG

ACAGGTGATGAGGGGTGGAAGGAGGTTGCTAAAGCAGCGACTCAGCGTCC

TAACATCATGGCGTATGTGCACGAAGGGGAAGGCGATGGATTGAAAGAGC

TTTTACATTTGATTGATCATATCTAGGTCCAGGGGTAAACGGCAGCTTGA

GGGCAACTTAAAAACTTAC
```

According to a second aspect of the invention there is provided a cell expressing at least one essential gene of the S9 segment of AHSV and that complements said essential gene(s) mutated in the ssRNA as disclosed herein, which thereby enables the replication of a vaccinal viral strain in the cell when infected with the ssRNA.

Most preferably said cell complements the function of said essential viral gene(s) carrying said mutation(s) thereby allowing the vaccinal viral strain to replicate in the cell. As will be appreciated by those skilled in the art, the ssRNA has been mutated such that the function of said essential gene(s) has/have been destroyed. By having a cell that complements the function of said essential viral gene(s), protein produced by said essential gene(s) is expressed from cellular mRNA, rather than from the ssRNA of the virus, and so the function of this gene is complemented by the cell. This ensures that all the essential proteins that are necessary for replication or propagation of the virus are present within the cell. Therefore, the vaccinal viral strain can freely replicate within the cell. However, if the vaccinal viral strain infects a cell other than the complementing cell, the protein product of said essential gene(s) will not be present and so the vaccinal viral strain will not be able to propagate. The vaccinal viral strain will undergo a single replication cycle, for example, in a vaccinated host.

In a preferred embodiment, said cell can be any cell which is suitable for being transfected with ssRNA and for culturing viral strains. The cell is a virally permissive cell. Preferably, the cell is a BHK 21 cell, a Vero cell, a 293T cell, a BSR cell (a clone of a particular BHK 21 cell), a HeLa cell, a C6/36 cell (a mosquito cell line derived from *Aedes albopictus*), or a KC cell (a midge cell line derived from the natural insect vector *Culicoides sonorensis*). More preferably, the cell is a BSR cell.

Reference herein to the term "vaccinal viral strain" means a viral strain that is suitable for being used in a vaccine for immunising a host that is normally affected by the wild-type virus. A vaccinal viral strain is one that is non-pathogenic and cannot cause infection. Therefore, it does not cause the disease that is normally associated with the wild-type virus. The concept of vaccinal viral strains is well known to those skilled in the art. For example, wild-type viruses can be attenuated or inactivated so that they generate an immune response in a host immunised with the attenuated or inactivated virus without causing full blown infection. This allows a host to mount an effective immune response if the host is subsequently exposed to the wild-type virus.

Accordingly, there is therefore also provided a cell infected with the ssRNA as herein disclosed.

According to a third aspect of the invention, there is provided a vaccinal viral strain comprising the isolated ssRNA as herein disclosed.

More preferably, said vaccinal viral strain is serotype specific and so comprises any one of the following: ASHV1, AHSV2, AHSV3, AHSV4, AHSV5, AHSV6, AHSV7, AHSV8 and AHSV9. More ideally, said vaccinal viral strain comprises a plurality of said serotypes, including any combination of AHSV1-9, including all of AHSV1-9.

Those skilled in the art will appreciate that use of the different serotypes enables the vaccine of the invention to provide maximum protection against each of the viral strains—whose virulence can vary, for example AHSV 4 is shown to be more virulent in mouse models than AHSV 1 and so strain AHSV4 may be preferred in the vaccine of the invention over AHSV1 etc.

Thus using our technology we have created replication-competent, propagation-disabled virus particles, with capsid proteins from all AHSV serotypes. Moreover, we have produced high titres of these particles in complementary cell lines. Notably, passaging in a complementary cell line did not reveal changes in the mutated S9, which would restore any of the mutated ORFs. Further, replication efficiencies were close to wild-type AHSV thus generating substantial protein levels for vaccine development. This therefore represents a stable, superior and efficient vaccine therapy.

According to fourth aspect of the invention, there is provided the isolated ssRNA as herein disclosed or the vaccinal viral strain comprising the isolated ssRNA for use in therapy. More preferably, said isolated ssRNA or vaccinal viral strain is used for vaccinating a non-human animal against AHSV.

In a preferred embodiment of the fourth aspect of the invention, said non-human animal is selected from the group comprising or consisting of horses, ponies, mules, donkeys or zebras.

According to a fifth aspect of the invention, there is provided a pharmaceutical composition comprising the isolated viral ssRNA as herein disclosed or the vaccinal viral strain comprising the isolated ssRNA, in combination with a pharmaceutically acceptable carrier, adjuvant or vehicle.

The compositions should ideally be sterile and contain a therapeutically effective amount of the isolated ssRNA or vaccinal viral strain in a unit of weight or volume suitable for administration to a subject. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism.

Formulations for administration include those suitable for oral, rectal, nasal, bronchial (inhaled), topical (including eye drops, buccal and sublingual), vaginal or parenteral (including subcutaneous, intramuscular, intraperitoneal, intravenous and intradermal) administration and may be prepared by any methods well known in the art of pharmacy.

The preferred routes of administration means the therapeutic is formulated for intravenous, parenteral, oral, nasal, bronchial or topical administration.

The composition may be prepared by bringing into association the isolated ssRNA or vaccinal viral strain of the invention and the carrier. In general, the formulations are prepared by uniformly and intimately bringing into association the active agent with liquid carriers or finely divided solid carriers or both, and then, if necessary, shaping the product. The invention extends to methods for preparing a pharmaceutical composition comprising bringing the isolated ssRNA or vaccinal viral strain of the invention in conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, formulations may be made into a cream, ointment, jelly, solution or suspension etc. Cream or ointment formulations that may be used for the drug are conventional formulations well known in the art, for example, as described in standard text books of pharmaceutics such as the British Pharmacopoeia.

Compositions of the invention may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

The precise amount of the isolated ssRNA or vaccinal viral strain of the present invention which is therapeutically effective, and the route by which it is best administered, is readily determined by one of ordinary skill in the art by comparing the tissue level of the vaccine to the concentration required to have a therapeutic effect.

According to a sixth aspect of the invention, there is provided a combination therapeutic comprising a pharmaceutical composition according to the invention and one or more different additional anti-viral agents.

Those skilled in the art will appreciate that the additional anti-viral agents are conventionally known.

According to a seventh aspect of the invention there is provided a method for vaccinating a non-human animal against a AHSV, the method comprising delivering or administering an effective amount of the isolated ssRNA as defined herein or the vaccinal viral strain comprising said isolated ssRNA, to a non-human animal.

In a preferred method of the invention, said non-human animal is selected from the group comprising or consisting of: horses, ponies, mules, donkeys or zebras.

According to an eight aspect of the invention, there is provided kit comprising the isolated ssRNA as disclosed herein and a cell that complements said essential gene(s) mutated in the ssRNA.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

The invention will now be described, by way of example only, with reference to the following figures and tables wherein:—

BRIEF DESCRIPTION OF THE DRAWINGS

FIG. 1. Genetic and phenotypic analysis of AHSV serotypes. The upper panel represents the analysis of plaque morphology, obtained by infection of BSR cells and incubated for 48 hours. The lower part represents the strategy for choosing the best replicating AHSV serotype with large plaque phenotype, high titres and lowest genetic variability to serve as a backbone for reverse genetics;

FIGS. 2A-2C. Establishment of reverse genetics for AHSV1. (A) Minimum requirements for primary replication of AHSV1. BSR cells were transfected in triplicates with the set of expression plasmids, indicated on the first row, followed by second transfection of 10 capped AHSV1 T7-RNA transcripts (S1 to S10), as indicated on the second row. The estimated infectivity is presented as PFUs per 1 µg of total T7 RNAs at 48 hours post 2nd transfection. The lowest panel is a representative picture of plaques obtained by double transfection for each experiment indicated above. (B) Plaque assays of wild type (wt) and rescued recAHSV1 stocks on BSR cells at 48 hours post infection. The infectious titres are presented as range, obtained from 5 independent passaging (for wtAHSV1) or rescue (for recAHSV1) experiments. (C) Pattern of genomic dsRNA purified from infected BSR cells with wtAHSV1 and recAHSV1 was analysed on a 9% non-denaturing PAGE. The positions of the genomic dsRNA segments are indicated on the right;

FIGS. 3A-3C. A stable cell line expressing VP6 complements VP6/NS4-deficient AHSV1. (A) The complementary cell line expressing AHSV1 VP6 was created by electroporation of BSR cells and selection of the VP6-expressing colonies. The selected clone was passaged for 30 times at 1:20 dilutions and equal amount of cells of indicated passages was analysed by immunoblotting using VP6-specific antibody. (B) Schematic diagram of the complementation-assisted defective AHSV1 rescue. BSR-VP6 cells were transfected with the set of five expression plasmids (VP1, VP3, VP4, VP6 and NS2), followed by transfection of 10 AHSV1 T7 RNA transcripts, where S9 is replaced by S9multistop, which is deficient in VP6/NS4 expression. VP6 is complemented in trans resulting in single-round replication, but non-propagating defective virus. (C) BSR-VP6 cells were transfected with the set of 5 expression plasmids (80 ng of each), followed by second transfection of total 50 ng of 10 capped AHSV1 T7-RNA transcripts, where S9 is replaced by S9multistop, which is deficient in VP6/NS4 expression. The transfected wells were fixed and stained at 56 hours post 2nd transfection. The mock and recAHSV1 rescue are used as controls at the same conditions as def-AHSV1;

FIGS. 4A-4B. VP6-complemented well-replicating defective reassortant AHSV variants obtained by combination of different segments. (A) Schematic representation of selected defective re-assortants of AHSV2-9. The upper panel indicates the segments that had been exchanged in order to achieve high titres and large-plaque phenotype in BSR-VP6 cell line. The cartoons of defective AHSV particles illustrate the origin of four major structural proteins as being of AHSV1 (blue) or other serotype (red). The red-coloured dsRNA segments indicate the exchanged segment (S2, S3, S6, S7 and S10). The serotypes obtained for each re-assortment group is indicated at the lower panel. (B) Pattern of genomic dsRNA purified from infected BSR-VP6 cell line with wtAHSV1, recAHSV1 and defective AHSV variants (5th passage at MOI 0.1 on BSR-VP6 cell line) was analysed on a 9% non-denaturing PAGE. The positions of the genomic dsRNA segments are indicated on the right. The wt-S9 dsRNA position is indicated on the left, whereas S9multistop dsRNA of defective AHSV variants is indicated in red and marked by red asterisk (*) on the gel. The red arrows on the gel correspond to the exchanged segments used for the rescue of defective AHSV variants;

FIGS. 5A-5D. VP6/NS4-deficient viruses are capable of growth in complementing BSR-VP6 cell line, but not in normal BSR, insect KC or equine E. Derm cells. (A) Virus growth kinetics in complementing BSR-VP6 cell line. BSR-VP6 cells were infected at an MOI 0.1 with the set of indicated viruses and analysed by plaque assay on BSR-VP6 cells at 0, 24, 48 and 72 hours post-infection. The final titre of each virus is indicated at the right panel. (B) Virus growth kinetics in normal BSR, insect KC and equine E. Derm cells. Three cell lines were infected at an MOI 5 (BSR), 2.5 (KC) and 10 (E. Derm), washed twice and analysed by plaque assay on BSR-VP6 cells at 0, 24, 48 and 72 hours post-infection;

FIGS. 6A-6C. Protection of IFNAR−/− mice with def-AHSV1 and def-AHSV4 from homologous challenge infection with wt AHSV1 and wt AHSV4 viruses. (A) Survival plots of adult IFNAR−/− mice (6 per group) immunized with 106 PFUs of def-AHSV1 and def-AHSV4 and challenged with 105 TCID50 of homologous wt AHSV strains. RNAemia in blood (B) and organs (spleen, liver, brain) (C) in indicated groups of animals presented as inverted graph of Ct values obtained by RT-qPCR. The values of Ct above 40 were considered as negative. Each dot corresponds to one analysed animal sample;

FIG. 8. Seroconversion of animals after vaccination. The immune responses of the vaccinated animals were monitored by VP7 group specific competitive ELISA. Animals in group A (left panel) and group B (right panel) were vaccinated twice with ECRA.A4 or ECRA.A1/4/6/8 respectively, 21 days apart and compared to group C (mock vaccinated animals);

FIGS. 9A-9B. Clinical protection in vaccinated ponies after virulent virus challenge. Clinical signs were monitored from day 36 onwards. (A) Clinical signs were scored for vaccinated groups A and B (up to 18 days) and control group (up to 10 days) (upper, middle and lower panels, respectively). (B) Severe clinical signs after challenge in both control animals were evident as oedema of the eyelids and supraorbital fossae (left) and conjunctivitis (right);

FIGS. 11A-11B. Details of the multiple mutations in Segment 9 used in the ECRA vaccine strains (group A ECRA.A4 virus and group B a cocktail of ECRA.A1/4/6/8) used to generate the data in FIG. 7-10;

Figure 6B:
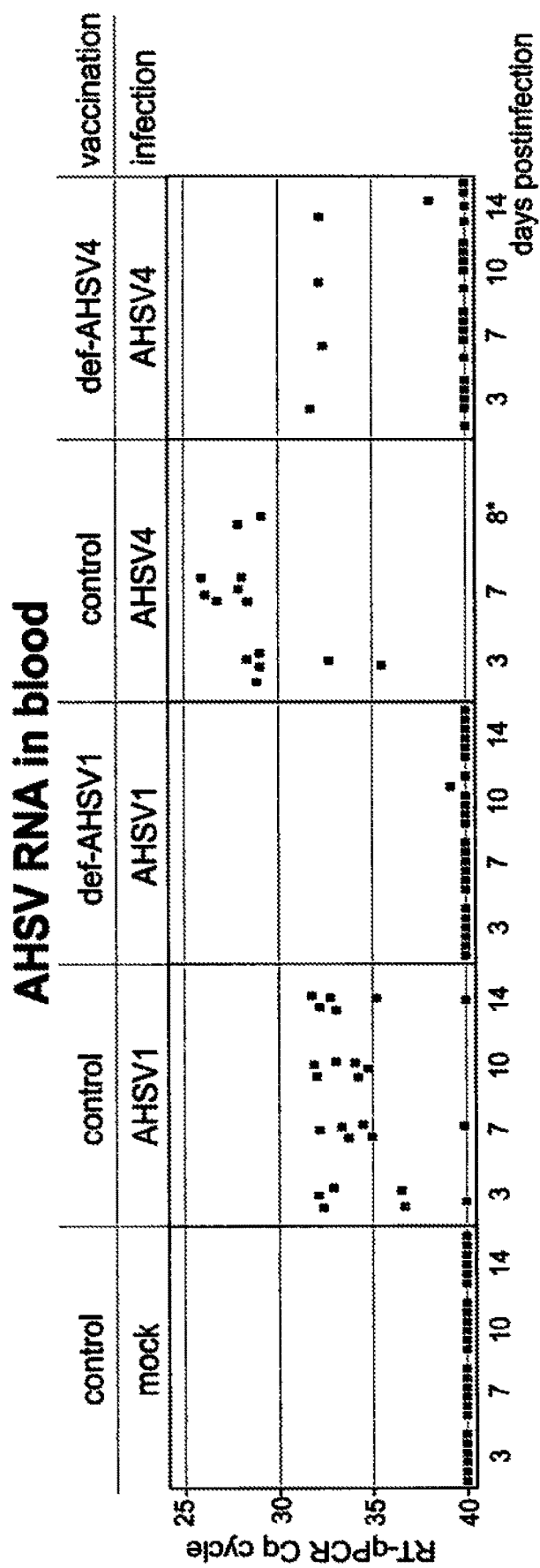

Table 1. Serum neutralization activity in ponies after vaccination. Neutralizing activity in sera was determined by plaque reduction assay at Day 35 (one day before challenge) against AHSV serotypes 1, 4, 6 and 8 as indicated. Titers are expressed as the highest dilution of serum allowing reduction of 50% of number of plaques. Not determined (nd) and not detected (-) are indicate; and Table 2. Serum neutralization activity in ponies after virulent virus challenge. Neutralizing antibody titers of vaccinated animal sera were determined by SN assay at Days 44 and 60 (8 and 24 days post challenge) against serotypes AHSV 1, 4, 5, 6 and 8. Titers were expressed as the reciprocal of the highest dilution of sera allowing complete neutralization. SN assays were not performed of the control animal sera at day 44. Both C1 and C2 ponies were euthanized respectively at 11 days and 10 days' post challenge due to severe AHS symptoms. Not determined (nd) and not detected (-) are indicated.

Methods & Materials

Cells and Viruses.

BSR cells (BHK-21 subclone) were maintained in Dulbecco modified Eagle medium (DMEM, Sigma) supplemented with 5% fetal bovine serum (FBS, Invitrogen). The stable cell line BSR-VP6 was grown in DMEM-5% FBS supplemented with 7.5 µg/ml of puromycin (Sigma). Equine dermal (E. Derm) cells (NBL-6, ATCC CCL-57) were cultured in minimum essential medium eagle (MEM, Sigma) supplemented with 10% FBS and 1% non-essential amino acids. Mammalian cell lines were cultured at 37° C. in a 5% CO2 humidified atmosphere. Insect KC cells, derived from *Culicoides* (24), were maintained at 28° C. in Schneider's insect medium supplemented with 10% FBS.

ASHV serotypes 1 to 9 were kindly supplied by Dr. Zientara (ANSES France). All AHSV serotypes were passaged once in BSR cells, titrated and used for subsequent experiments.

Plasmids

For AHSV1 RG system, the coding regions of corresponding segments were inserted in pCAG-PM vector (18) using AflII and PacI restriction sites. Corresponding expression plasmids were designated as pCAG-AHSV1VP1, pCAG-AHSV1VP3, pCAG-AHSV1VP4, pCAG-AHSV1VP6, pCAG-AHSV1VP7, pCAG-AHSV1NS1 and pCAG-AHSV1NS2 and confirmed by sequencing. T7 plasmids for AHSV transcripts were generated using a sequence-independent cloning system as previously described (17). Briefly, purified dsRNAs from concentrated viruses were ligated to a self-annealing primer before RT-PCR amplification with adaptor primer. Each cDNA amplified from AHSV segments was cloned into pUC19 vector and sequenced.

AHSV1 S9multistop mutant was created by gene assembly and mutations at positions 288-304 (3stop codons+NS4 frameshift), 377-386 (3 stop codons), 590-608 (3 stop codons) and 872-877 (2 stop codons) were introduced. The sequence was confirmed and available upon request.

Development of BSR-VP6 Cell Line Expressing AHSV1 VP6 Constitutively

The complementary cell line expressing AHSV1 VP6, BSR-VP6, was generated as described previously (18) with some modifications. Briefly, BSR cells were transfected by electroporation at 240V and 975 µF with AHSV1-VP6 expressing vector, pCAG-AHSV1VP6. After electroporation, suspension of cells was seeded onto 150 mm culture plates and VP6 expressing colonies were selected in the presence of 7.5 µg/ml of puromycin. Surviving clones were tested by immunoblotting analysis, and the best-expressing clone was used for the rescue of VP6-defective viruses. Expression of AHSV1 VP6 was assessed by SDS-PAGE and Western blotting using polyclonal guinea pig antiserum raised against AHSV6 VP6.

Recovery of wt AHSV1 virus from T7 RNAs. The T7 promoter and exact 3' end containing DNAs were used as templates in equimolar proportions to produce a mixture of 10 capped T7 RNAs for AHSV1 using mMESSAGE mMACHINE T7 Ultra f288 (Ambion) according to the manufacturer's instructions. For the rescue of recAHSV1, BSR cells at 50% confluence in 12-well plates were transfected with set of expression plasmids encoding for AHSV1 VP1, VP3, VP4, VP6, VP7, NS1 and NS2 in different combinations (80 ng of each plasmid per well). At 16 hours post-transfection, transfected monolayers were transfected again with a total 500 ng of all 10 capped RNA transcripts. To assess the RNA infectivity, 4 hours post second transfection the monolayers were overlaid with 1.5% agar in MEM, containing 1% FBS and incubated for 2-3 days at 35° C. until the formation of plaques. Alternatively, to collect a rescued virus, the transfection media was replaced with DMEM, containing 1% FBS and incubated for 2-3 days until appearance of CPE.

Recovery Def-AHSV from T7 RNAs

For rescue of def-AHSV1, BSR-VP6 cells at 50% confluence in 12-well plates were transfected with 5 pCAG plasmids encoding for VP1, VP3, VP4, VP6 and NS2 (80 ng each). At 16 hours post-transfection, BSR-VP6 monolayers were transfected with a total 500 ng of 10 capped AHSV1 RNA transcripts: S1-8, S10 and S9multistop. To obtain reassortant def-AHSVs, several segments were used to replace parental AHSV1. Each defective virus was plaque-purified and titrated on BSR-VP6 cells. To assess stability, each defective virus was passaged at least 5 times in BSR-VP6 cells at MOI of 0.1. The analysis of dsRNA profile and RT-PCR/sequencing were used to confirm the integrity of introduced AHSV segments.

In Vitro Growth Kinetics of AHSV

The in vitro growth kinetics of wt AHSV and defective viruses were determined in BSR-VP6, BSR, KC and E. Derm cells following infection for 1.5 hours with an MOI of 0.1, 5, 2.5 and 10, respectively. After infection, inoculum was removed and cells were washed twice with media supplemented with 1% FBS. At 0, 24, 48 and 72 hours post-infection, the supernatant was harvested and the titer was determined by plaque assay on BSR-VP6 cells. Each experiment was performed in triplicates and repeated twice.

Mice

Thirty IFNAR−/− mice on a C57BL/6 genetic background were obtained from the specific pathogen free breeding unit of the FLI and assigned into 5 groups; male and female animals were distributed equally. Six mice each were vaccinated twice three weeks apart with 106 PFUs (100 µl) of the def-AHSV1 and def-AHSV4 viruses, respectively, and infected 21 days after the second immunization with 105 50% tissue culture infective doses (TCID50) in 100 µl of either AHSV serotype 1 (def-AHSV1 group) or 4 (def-AHSV4 group). Twelve mice were mock-vaccinated with phosphate-buffered saline (PBS), six of them were infected with AHSV1 and six with AHSV4. Six further mice were kept as controls.

All mice were weighed daily for 10 days after vaccination and infection and examined for clinical signs, animals showing severe symptoms were euthanized immediately, all remaining infected animals 2 weeks after challenge infection and untreated control animals after 3 weeks. All mice were blood sampled at 3, 7 and 10 days after infection. At autopsy, blood, spleen, liver and brain samples were taken and organ samples were homogenized in 1 ml serum-free MEM. RNA from 20 µl blood or 100 µl tissue homogenate was extracted using the King Fisher 96 Flex (Thermo Scientific, Braunschweig, Germany) in combination with the MagAttract Virus Mini M48 Kit (Qiagen, Hilden, Germany) according to the manufacturer's instructions and analysed by a VP7-based real-time RT-PCR assay (25) combined with an internal control system targeting the housekeeping beta-actin gene (26).

Ponies

Figure 11A:
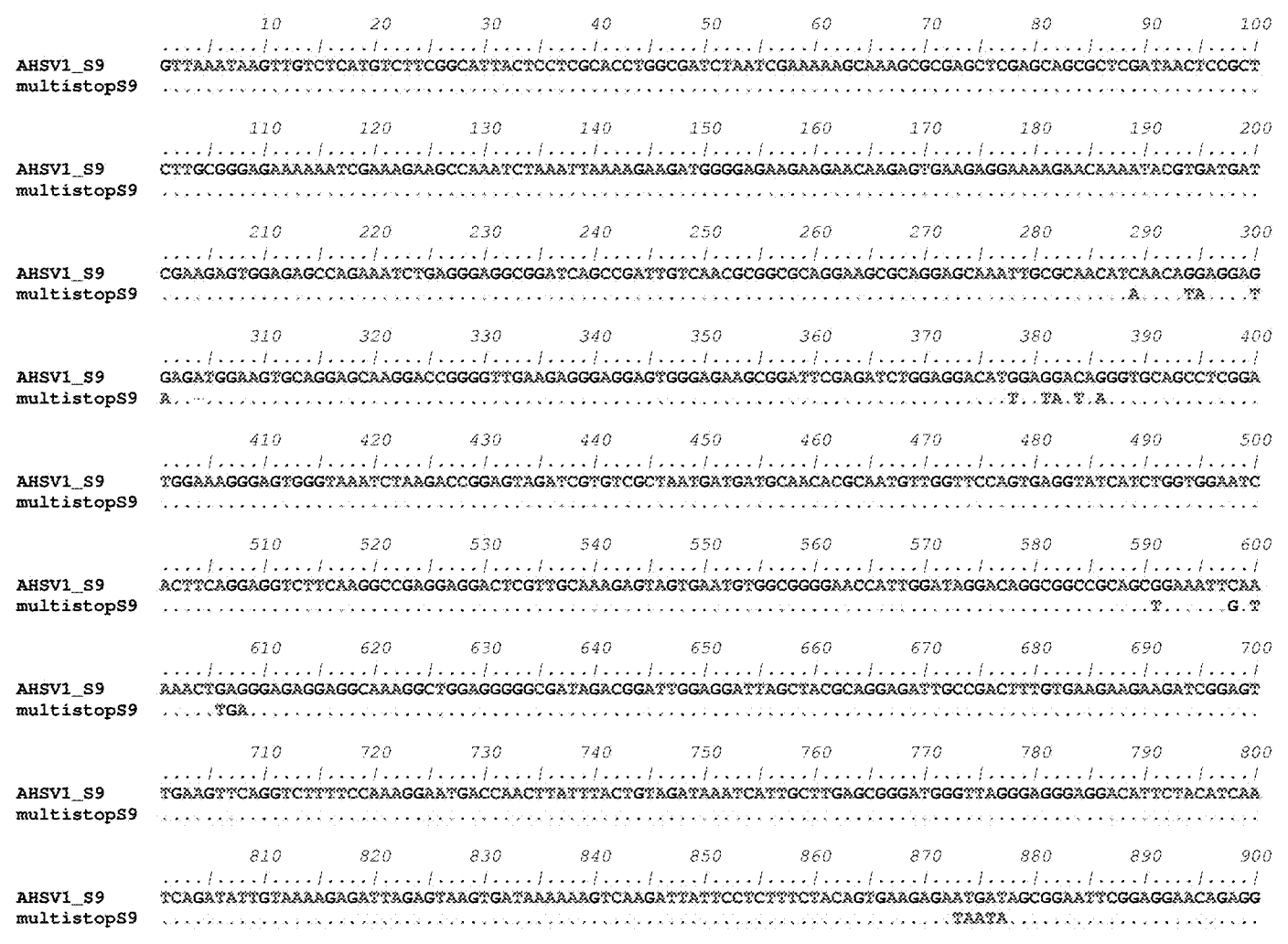

FIG. 11 shows details of the multiple stop codons introduced into Segment 9 and used for the following vaccination of ponies, the early passaged ECRA.AHSV stocks (1-2 passages in BSR-VP6 cells) were amplified in BSR-VP6 cells at an MOI 0.1 in antibiotic-free media. The resulting ECRA.AHSV stocks were supplemented with 10% trehalose (Sigma), aliquoted, frozen in liquid nitrogen and stored at −80° C. until vaccination. The aliquots of frozen stock were titrated on BSR-VP6 cells and tested for the absence of replication in naïve BSR cells for at least 3 blind passages by visualization of the absence of typical cytopathic effects (CPE) and confirmation by RT-PCR. The mock-vaccine dose was prepared from equivalent amount of BSR-VP6 cells via lysis by sonication. Vaccine stability was tested after different storage conditions, more specifically different temperatures (+4° C., −20° C., and −80° C.), direct freezing or freezing in liquid nitrogen, supplementing or not with trehalose (Sigma) at 10% final concentration.

Monoserotype and Cocktail ECRA.AHSV Vaccination in Ponies.

Two groups of 4 animals were subcutaneously inoculated with ECRA vaccine strains, group A with ECRA.A4 virus ($1\times10^7$ PFU/animal, Group A) and group B with a cocktail of ECRA.A1/4/6/8 ($1\times10^7$ PFU of each serotype/animal) at day 0. In addition, 2 animals were mock-vaccinated with uninfected cell lysates (Group C). A booster injection was given 21 days after the first vaccination. At day 36 or two weeks after the booster vaccination, all animals were challenged intravenously with $2\times10^6$ $TCID_{50}$ of a virulent isolate of AHSV4 (Morocco 1990). Challenge virus stock was obtained after 5 passages on Vero cells of a spleen extract from an AHSV4 infected horse and one additional passage either on Vero or KC cells: each horse was challenged with $10^6$ $TCID_{50}$ obtained on Vero cells and $10^6$ TCID50 recovered from KC cells). Whole-blood and serum samples of all animals were taken at regular intervals before and after vaccination and challenge. This study was performed in strict accordance with the French guidelines and recommendations on animal experimentation and welfare. The protocol was approved by the ANSES/ENVA/UPEC Animal Ethics Committee.

RNA Extraction and RT-PCR.

RNA was extracted from blood samples and from organs (spleen, lung and heart) homogenized in 10% w/v PBS with the QIAamp viral RNA kit and the Qiacube robot (QIAGEN). Genomic double-stranded RNA extracts were heat treated prior to addition to the RT-PCR reaction mix (addition of 10% DMSO and heating at 95° C. for 5 minutes). Real-time AHSV RT-PCR targeting the 51 segment was performed in two times in three replicates, with modifications necessitated for the RT-PCR kit (AgPath-ID™ One-Step RT-PCR Kit (ThermoFisher Scientific) instead of SuperScript III/Platinum Taq One-Step qRT-PCR Kit) and to the cycling conditions in StepOne or AB7300 thermocycler: 45° C. for 10 min, 95° C. for 10 min followed by 45 cycles of 95° C. for 10 s, 55° C. for 30 s and 72° C. for 30 s. Cycle threshold (Ct) values were measured and values above a threshold of 40 were considered as negative.

Serology of Monoserotype ECRA.A4 and Cocktail ECRA.A1/4/6/8 Trials.

Serum samples were analysed by a commercially available competitive ELISA AHSV VP7 Antibody Test kit (ELISA Ingezim AHSV Compaq) according to manufacturer's instructions. Serological status was defined as positive (≥50%), doubtful (>45% and <50%) or negative (≤45%).

To detect neutralizing antibody response, standard serum neutralization (SN) assays or plaque reduction assays were used. For standard SN assays, serum samples, as well as positive and negative control sera, were serially diluted in 96 well plates and mixed with 100 infectious AHSV particles (for AHSV 1, 4, 5, 6 or 8) for 60 minutes at 37° C. After the addition of $10^4$ Vero cells per well, plates were incubated for 7 days at 37° C., 5% $CO_2$, fixed with 4% PFA and stained with methylene blue 0.5%. The neutralizing titers were defined as the highest dilution of sera affording complete protection of the cell culture. For plaque reduction assays, serum samples were serially diluted in 96 well plates and about 25 infectious AHSV particles were added to each well. All dilutions were performed in triplicates. The serum-virus mixture was incubated for 2 hours on a shaker at room temperature and added to confluent monolayers of BSR cells in 12 well plates for 1 hour. Following incubation, the infected cells were overlaid with 0.6% Avicel (IMCD LTD) in MEM and incubated for 3 days. The neutralizing titers were defined as the highest dilution of sera exhibiting 50% reduction in viral plaques, calculated from the number of plaques observed in each well compared to controls (FBS and serum from control animals).

Clinical Monitoring

Ponies were monitored on a daily basis during 8 days after vaccination and 3 weeks after challenge for development of AHSV clinical signs. General signs (behavioural modifications, hyperthermia, cardiac rate and breathing rhythm, sudation), as well as signs of oedema, abnormal bleeding (petechiae), dyspnoea, nasal discharge and conjunctivitis were recorded and scored according to the following criteria:

Behaviour: Normal—0 pt, Apathy—1 pt, Depression—2 pt, Prostration—3 pt General parameters: rectal temperature (T)=Normal—0 pt, 39° C.≤T≤40° C.—1 pt, 40° C.<T—3 pt; cardiac rate=Normal—0 pt, >50—2 pt; breathing rhythm=Normal—0 pt, >25—2 pt Specific signs: Oedema—1 pt per location (eyelids, supraorbital fossa, lips, head, neck, trunk or disseminated), nasal discharge—1 pt per type of secretion (serous, mucous, purulent, haemorrhagic), petechial lesions—1 pt per location (conjunctivitis, oral cavity, skin), dyspnoea—1 pt, cough—1 pt, conjunctivitis—1 pt, abnormal sudation—1 pt, colic—1 pt.

Results

Establishment of Reverse Genetics for ASHV

Figure 1:
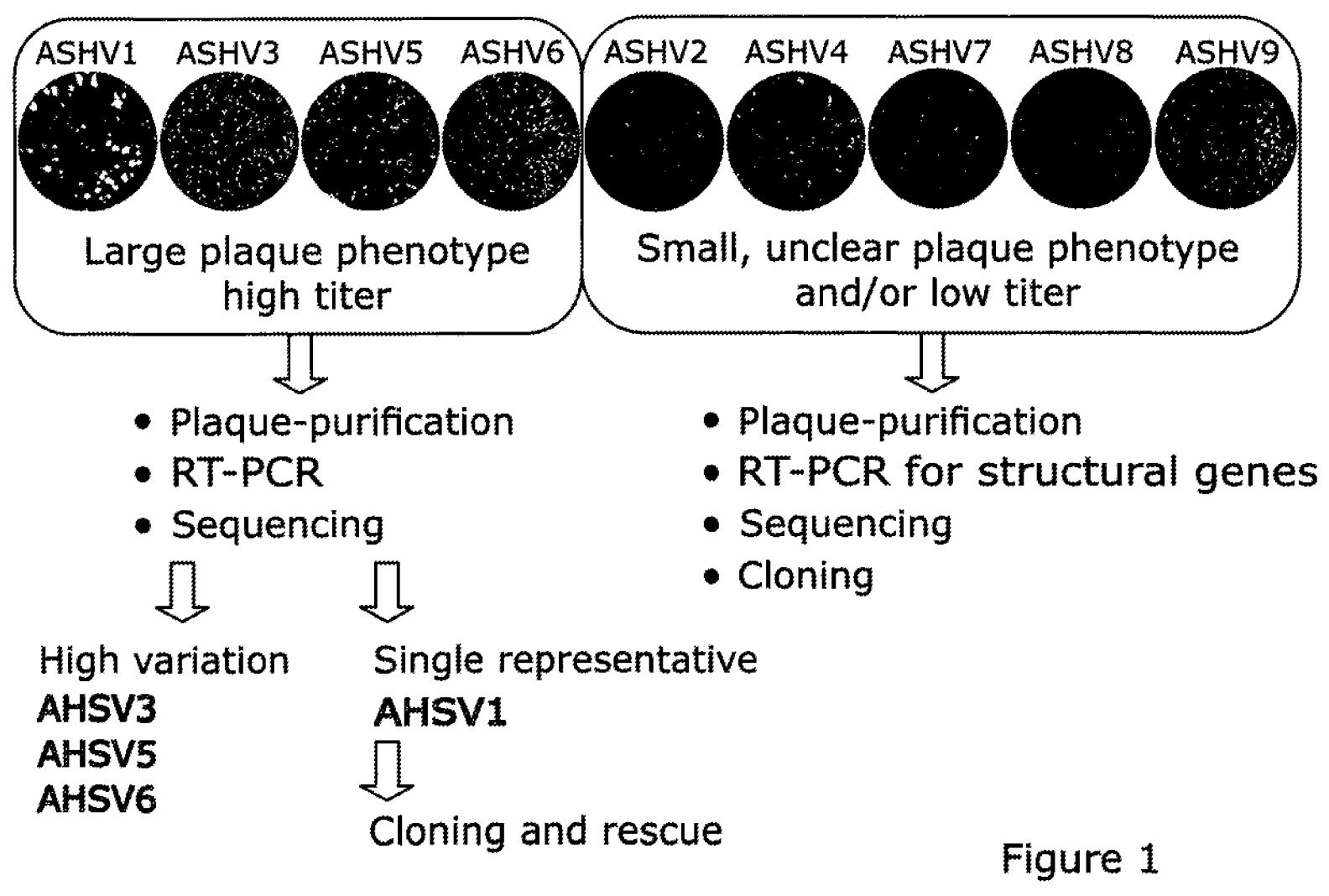

The efficient and fast virus reverse genetics (RG) is the key to the understanding of molecular mechanisms via manipulating the viral genome. The previously published AHSV RG consisted to mixed serotype transfection, namely six expression plasmids of AHSV6, followed by 10 T7-RNA transcripts of AHSV4 (23). This combination was found to be insufficient for molecular manipulations due to the low rescue efficiency and insufficient recombinant virus titers (<106 PFU/ml). Therefore we first aimed at finding a well-replicating AHSV strain forming uniform large plaques, which could be used as a backbone for the efficient RG system. First, all nine AHSV serotypes were tested on BSR cells to assess infectious titers and plaque phenotypes (FIG. 1). Two distinct groups of AHSV serotypes were observed: large defined plaque phenotype and high titre (AHSV1,3,5,6) and small/undefined plaque phenotype (AHSV2,4,7,8,9) with low titres (AHSV7). Four well-replicating AHSV serotypes (AHSV1,3,5,6) were tested for the genetic stability via sequencing of several plaque-purified isolates. Three of the analysed serotypes (AHSV3,5,6) were excluded at this point due to the high genetic diversity, that could complicate the development of the single genome-derived RG system. One plaque-purified AHSV1 was chosen as the most promising RG candidate since this strain has demonstrated both the high titres ($5\times108$ PFU/ml), large uniform plaque phenotype and single representative clones revealed by sequencing for all 10 segments.

The recovery of full copies of 10 AHSV1 RNA segments was performed by sequence-independent method. For each segment, a T7 promoter-derived plasmids with exact 3'-end were generated to produce 10 capped T7 RNA transcripts. The protein-coding sequence of VP1, -3, -4, -6, -7 and NS1, -2 was used to generate expression plasmids under the control of pCAG promoter. For related BTV, it has been demonstrated that transfection by a set of VP1, -3, -4, -6, NS1 and -2 followed the next day by the transfection of 10

T7 RNA transcripts was sufficient to obtain efficient BTV rescue. For ASHV1 recovery we have tested several conditions that mimic the preformation of primary replication complex. First, transfection of 3 to 7 expression plasmids was performed as shown on FIG. 2A. After the second transfection with 10 capped T7-RNA transcripts, agar-overlaid BSR monolayers were used to assess the efficiency of AHSV1 rescue. Different combinations of expression plasmids in the first transfection have revealed the sufficient set of 5 plasmids (VP1, -3, -4, -6 and NS2), which was used throughout all the subsequent experiments (FIG. 2A). Media-overlaid BSR monolayers were monitored for CPE to harvest the recombinant ASHV1 (recAHSV1). Rescued virus was amplified in naïve BSR cells, reaching the titers $4 \times 10^8$ PFU/ml. The plaque morphology was similar to AHSV1 parental virus (FIG. 2B). The analysis of extracted dsRNAs on a native polyacrylamide gel showed the typical AHSV1 genomic dsRNA profile (FIG. 2C). Taken together, the efficient AHSV1 RG system required transfection of 5 expression plasmids followed by transfection of 10 AHSV1 T7-RNA run-off transcripts.

A Stable Cell Line Expressing AHSV1 VP6 that Complements VP6/NS4-Deficient AHSV

Next, we aimed at developing a defective AHSV platform to transfer the virus-based experiments to the lower containment level to perform functional and structural studies. The ability of trans-complementation of VP6 from the related BTV has led to the development of the VP6-deficient mutant viruses that are able to replicate in complementary cell line, but not in parental BSR or insect KC cells. We developed further this technology and created AHSV1 VP6 expressing BSR cell line (BSR-VP6) by electroporation of BSR cells with pCAG-AHSV1VP6, following the puromycin selection. The selected clone was stably expressing VP6 for 30 passages at low dilutions (FIG. 3A). The design of VP6-deficient AHSV was complemented with the disruption of NS4 ORF. The expression of NS4 has been shown to be dispensable for BTV replication in BSR cells. If this is the case for AHSV, the deletion of NS4 represents an additional attenuation step. To construct VP6/NS4-deficient AHSV1 (def-AHSV1), we introduced multiple nucleotide changes in S9 of AHSV1. Instead of deletions reported for VP6-deficient BTV viruses, we have introduced 11 stop codons (TAA or TGA) throughout the S9 gene disrupting the ORFs of VP6 and NS4, but retaining the length of the obtained S9multistop thus minimizing the genetic pressure on the defective AHSV1 rescue and replication. The absence of VP6 in def-AHSV1 was expected to be compensated by complementary cell line.

Figures 4A, 4B:
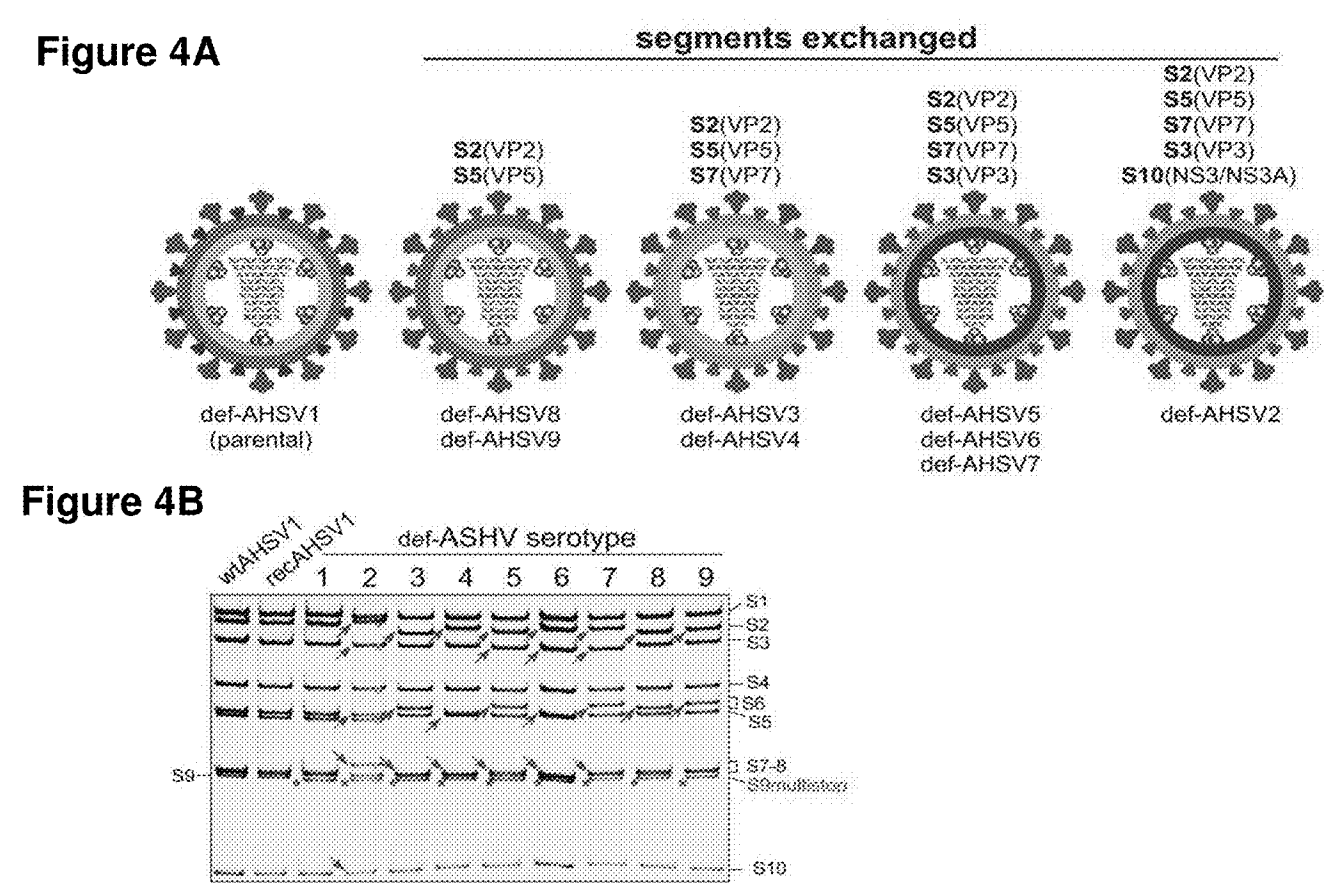

Using BSR-VP6 complementary cell line, def-ASHV1 was recovered by transfection of 5 expression plasmids followed by transfection of 10 capped T7 RNA transcripts, where S9 was replaced by S9multistop (FIG. 3B). After the second transfection, agar-overlaid BSR monolayers were used to assess the RNA infectivity, which was comparable to AHSV1 wt set of T7 RNAs (FIG. 3C). Media-overlaid BSR monolayers were monitored for CPE to harvest the recombinant def-ASHV1. Rescued virus was plaque-purified using BSR-VP6 cell line, and amplified once reaching the titers $8 \times 10^7$ PFU/ml (titrated on complementary BSR-VP6 cell line). The plaque morphology and analysis of extracted dsRNAs on a native polyacrylamide gel showed the expected dsRNA profile (FIGS. 3C and 4B). These results have confirmed that AHSV VP6 can be efficiently complemented in trans and NS4 is dispensable for AHSV replication in BSR cells.

Efficient Assembly of Chimeric AHSV Particles Requires Reassortment of Several Segments The ability of orbiviruses to reassort provides the possibility of recoating of the conserved replicase or inner core thus resulting in serotype-specific particles. Such particles may have a broad application spectra, such as vaccine candidates or safe platform for structural and molecular studies. It has been previously demonstrated that the exchange of AHSV VP2 only can drop the re-assortant virus titres up to 3 logs, resulting in impaired replication and/or particle instability. Therefore, we aimed to recoat the def-ASHV1 by using combinations of different segments from other serotypes in order to achieve a well-replicating candidates for all other 8 AHSV serotypes (2 to 9).

Initially, AHSV serotypes 2 to 9 exact-copy segments S2 (VP2), S6 (VP5), S7 (VP7), S3 (VP3) and S10 (NS3/NS3A) were cloned using a sequence-independent method. The amino acid sequence analysis of the major structural proteins of 9 AHSV serotypes revealed the conservation increases in the expected order: the least conserved VP2 (identity 13-71%, similarity 27-84%), followed by VP5 (identity 75-99%, similarity 90-99%), followed by VP7 and VP3 (identity >98%, similarity >99%). Analogously to AHSV1, T7 promoter and exact 3' end DNAs were generated to produce T7 RNA transcripts. For defective virus recovery, BSR-VP6 cells were transfected with 10 T7 RNAs of AHSV1, S9 was replaced by S9multistop and, depending on serotype, a combination of S2+S6, S2+S6+S7, S2+S6+S7+S3 or S2+S6+S7+S3+S10 was used to replace analogous segments of def-AHSV1. The final assessment for the resulting defective viruses was chosen to be a plaque size (clear plaques after 2-3 days of incubation at 35° C.) and final titre for the plague-purified viruses performed on BSR-VP6 cell line ($10^7$ PFU/ml and higher, as a wt reference strain). These requirements were chosen to minimize any possible pressure to avoid recombination and instability of the modified dsRNA genome. To meet the selected criteria, AHSV serotypes 2-9 have demonstrated different requirements (FIG. 4A). To develop well-replicating def-AHSV8 and def-AHSV9 the reassortment with only 2 segments encoding outer shell proteins VP2 and VP5 was required (S2+S6). The development of def-AHSV3 and def-AHSV4 has been possible by reassortment of 3 segments (S2+S6+S7), which included the middle-core protein VP7. Three more serotypes were created by reassortment with 4 segments (S2+S6+S7+S3) resulting in def-AHSV5, def-AHSV6 and def-AHSV7. This set was created by complete replacement of the major structural protein shell. Finally, to develop well-replicating reassortant defective virus for serotype 2, five segments (S2+S6+S7+S3+S10) were needed to be replaced to achieve high titres on complementary BSR-VP6 cell line, resulting in def-AHSV2. The poor rescue efficiency, small plaque phenotype and titres ranging $10^4$-$10^6$ PFU/ml have been observed for these defective viruses (AHSV2,3,4,5,6,7), if less than indicated above segments were used for reassortment, therefore they were excluded from following studies. The schematic representation of all selected defective viruses is summarized on FIG. 4A. All 9 defective viruses were passaged 5 times at MOI 0.1 in complementing BSR-VP6 cell line, confirming at each step that none of tested stocks was able to replicate on naïve BSR cells. The initial rescued and the final 5th passage virus stocks were used to extract dsRNA to assess the stability and integrity of reassortant defective viruses. All analysed viruses have demonstrated correct dsRNA mobility (FIG. 4B). In addition, RT-PCR and sequencing have also validated the authenticity of the segments in all 9 def-AHSVs.

Defective AHSVs do not Grow in AHSV Susceptible Cell Lines, but Reach High Titers in Complementary Cell Line To determine the growth kinetics of the panel of created defective viruses in complementary BSR-VP6 cells, we infected BSR-VP6 cells at low MOI and measured the titres at 24, 48 and 72 hours post-infection. Similar to wt AHSV1 virus, all 9 defective viruses were capable of replication in the complementary BSR-VP6 cells reaching titers in the range 107-108 PFU/ml and forming plaques at 2-3 days post-infection (FIG. 5A).

To confirm that both parental def-ASHV1 and eight reassortant viruses were incapable of growth in normal cells, the growth kinetics of each disabled virus was evaluated by infecting 3 cell lines (BSR, KC and E. Derm) at high MOI and measuring the virus titres at 24, 48, and 72 hours post-infection. The results obtained demonstrated that these disabled viruses were not able to grow in BSR, KC (insect) and E. Derm (equine) cell lines (FIG. 5B-D). To make sure there is no delayed replication, all def-AHSV infected cells (BSR, KC and E. Derm) were incubated for further 7 days, but no signs of infection was detected. Three strains of wt AHSV1 were used in this experiment: recAHSV1 (obtained by RG from exact-copy T7-RNAs), wtAHSV1 (second BSR-passage from original AHSV1 stock) and AHSVKC (passaged twice in KC cells at MOI 0.1). All three AHSV stocks showed similar results (data not shown), therefore only one (recAHSV1) is shown (FIG. 5). Taken together, we conclude that all nine defective viruses grow to high titers (between 107 and 108 PFU/ml) in complementary cell line, but do not produce particles in BSR, KC and E. Derm cells. These in vitro results demonstrate a great potential for these defective viruses to be used as perspective AHSV vaccine candidates.

Defective AHSV1 and AHSV4 Efficiently Protect IFNAR-/- Mice from Homologous Infection As a proof of principle, def-AHSV1 and reassortant def-AHSV4 were used to demonstrate the protection efficiency against AHSV infection in mice model. For that, adult IFNAR-/- mice were immunized twice with 106 PFUs of def-AHSV1 and def-AHSV4. After vaccination no adverse side effects were observed, the body weight showed no significant differences between immunized and control animals (max. 10% variation for all groups). Three weeks after the second immunization, immunized and control animals were challenged subcutaneously with AHSV1 and AHSV4. Non-vaccinated and infected with AHSV-4 mice started to lose weight from day 3 or 4 post challenge infection onwards, 4 animals were euthanized 7 days after infection (severe weight loss, rough hair, unresponsive) and the two remaining mice on day 8. Mice of all other groups showed no clinical signs (FIG. 6A).

The levels of RNAemia were measured for all mice at 3, 7 and 10 days after infection. No AHSV-specific RNA was detected in any mock-infected mice. Mice infected with AHSV4 had significantly higher AHSV RNA levels in comparison with mice infected with AHSV1 (FIG. 6B). This data correlates with mice survival times (FIG. 6A), suggesting that AHSV1 represents a less virulent serotype. In immunized animal groups, the levels of RNAemia were significantly reduced (FIG. 6B). The analysis of AHSV-specific RNA was combined with an internal control system targeting the housekeeping beta-actin gene, which was present in all collected blood samples (Ct 26-32).

Figure 6C:
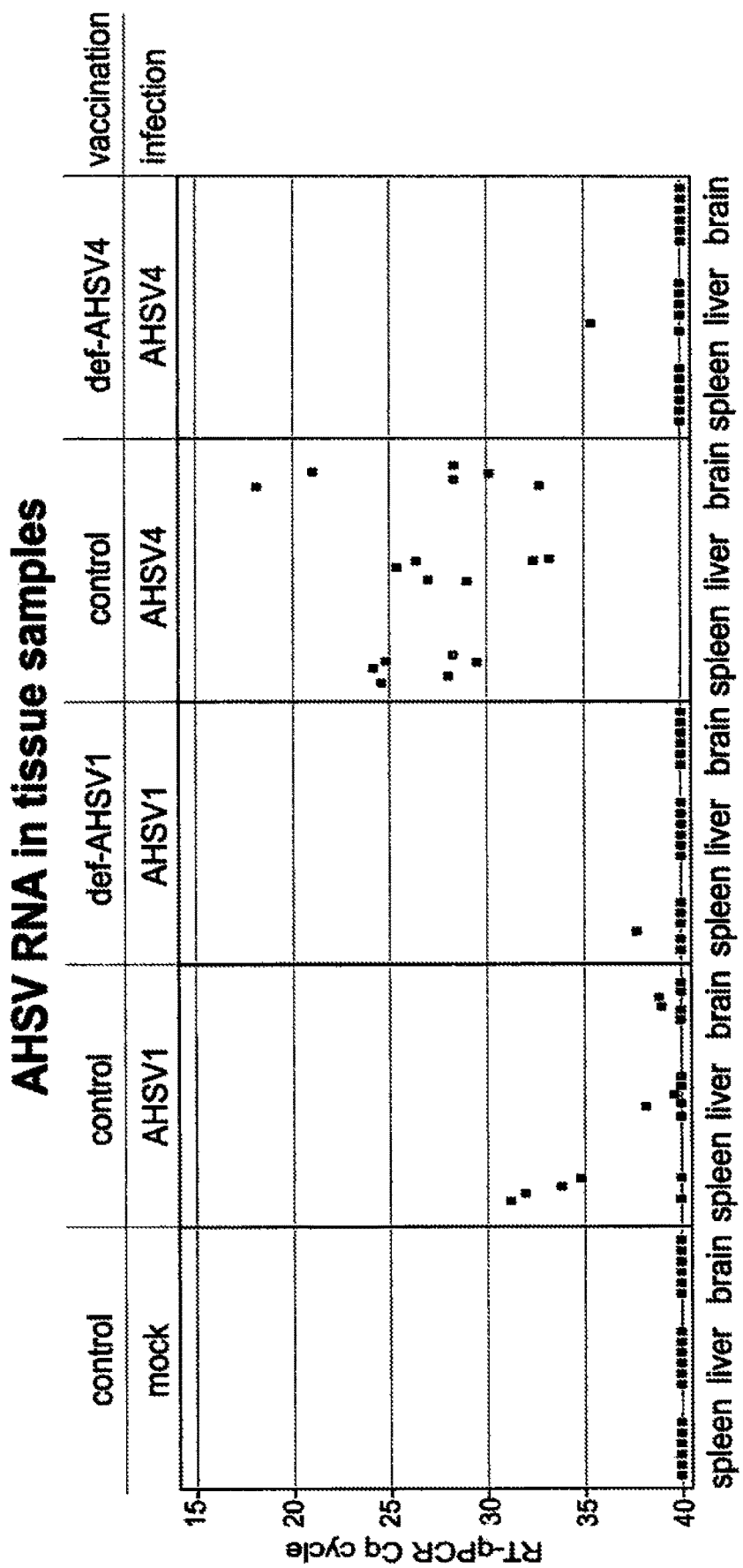

Spleen, liver and brain tissue samples were taken for RNA extraction and quantification as described in Materials and Methods. In agreement with the previous data (FIG. 6A-B), high loads of AHSV RNA were measured in all sampled organs for AHSV4 infected mice, whereas AHSV1 infected group demonstrated lower-to-none levels of AHSV RNA in analyzed organs. Vaccination with def-AHSV1 and def-AHSV4 prior to homologous AHSV challenge led to significant reduction of AHSV RNA levels in mice organs (FIG. 6C).

Protection indicators used in this study included body weight measurements, survival times, blood and tissue RNAemia. Non-immunized mice infected with AHSV1 and AHSV4 showed detectable levels of RNAemia, but AHSV1-infected mice had no mortality and weight loss in contrast to AHSV4. For this reason, RNAemia has been chosen as the main protection indicator to analyze the potency of the vaccine candidates.

Monoserotype and Cocktail Vaccination in Ponies

We evaluated the protective efficacies of these defective viruses in AHSV natural hosts, e.g. ponies. One monoserotype Entry Competent Replication-Abortive (ECRA) virus strains, formally known as DISC, for serotype AHSV4 (ECRA.A4) vaccine and one multivalent cocktail for serotypes 1, 4, 6 and 8 (ECRA.A1/4/6/8) vaccine were tested and ponies were challenged with a virulent AHSV4. Details of the multiple stop codons in S9 are shown in FIG. 11.

To assess the protective efficacy of ECRA.AHSV strains against AHSV4 infection in horses, two groups (A & B) of ponies were immunized twice with $1 \times 10^7$ PFU (ECRA.A4, group A) or a total of $4 \times 10^7$ PFU for cocktail (ECRA.A1/4/6/8, group B), each with $1 \times 10^7$ PFU def-AHSV. Uninfected cell lysates were inoculated to the control animals (group C). Due to restrictions on animal numbers (10 ponies), only one cocktail was tested in this study. First vaccination was performed at day 0 ("prime"), the same doses were inoculated for the booster vaccination at day 21 ("booster") and animals were then challenged with a virulent AHSV4 at day 36. Blood samples were collected periodically to monitor viral load and neutralizing antibody production from day 0 to day 44-46 for the group C (control animals) and from day 0 to day 60 for every vaccinated animal, except for animals A4 and B4. Both animals were subjected to monitoring for up to day 102, for possible long lasting viremia. The pony B4 which became pregnant during the trial was monitored for virus replication until the birth of the foal.

Figure 7A:
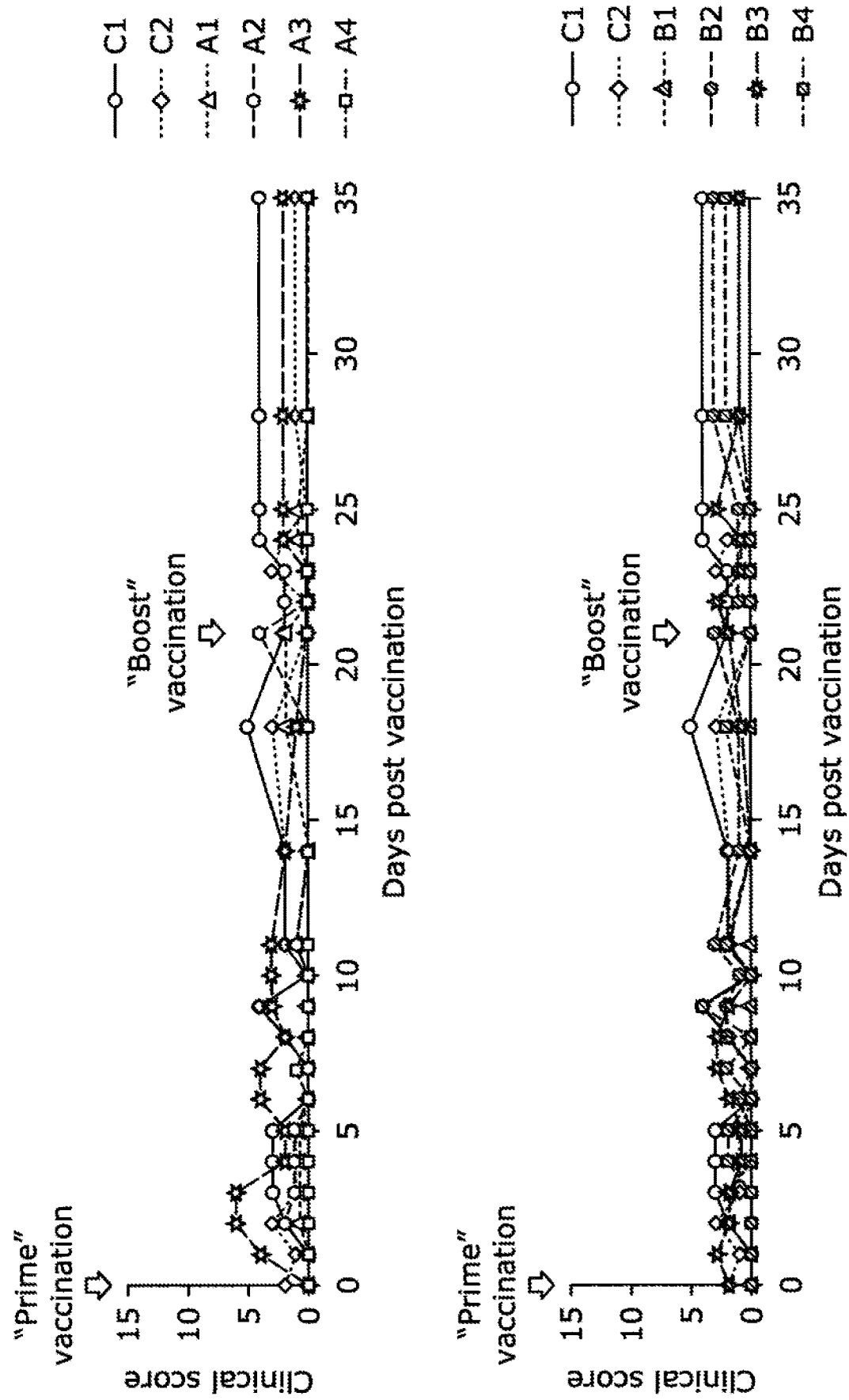
FIGS. 7A-7B. Clinical signs and viral replication in vaccinated animals. Animals were vaccinated twice at Day 0 and Day 21 (boost). (A) Clinical signs were scored based on body temperature, breathing rhythm, cardiac pulses, etc. Four animals were vaccinated with ECRA.A4 (group A; top panel), four with a cocktail of ECRA.A1/4/6/8 (group B; lower panel) and two animals were used as controls (C1 & C2). (B) AHSV genomic RNA in serum was determined by RT-PCR and expressed as Ct values. Virus load is represented by a colour gradient from green (ND: not detected) to red (Ct less than 25)
Figure 7B:
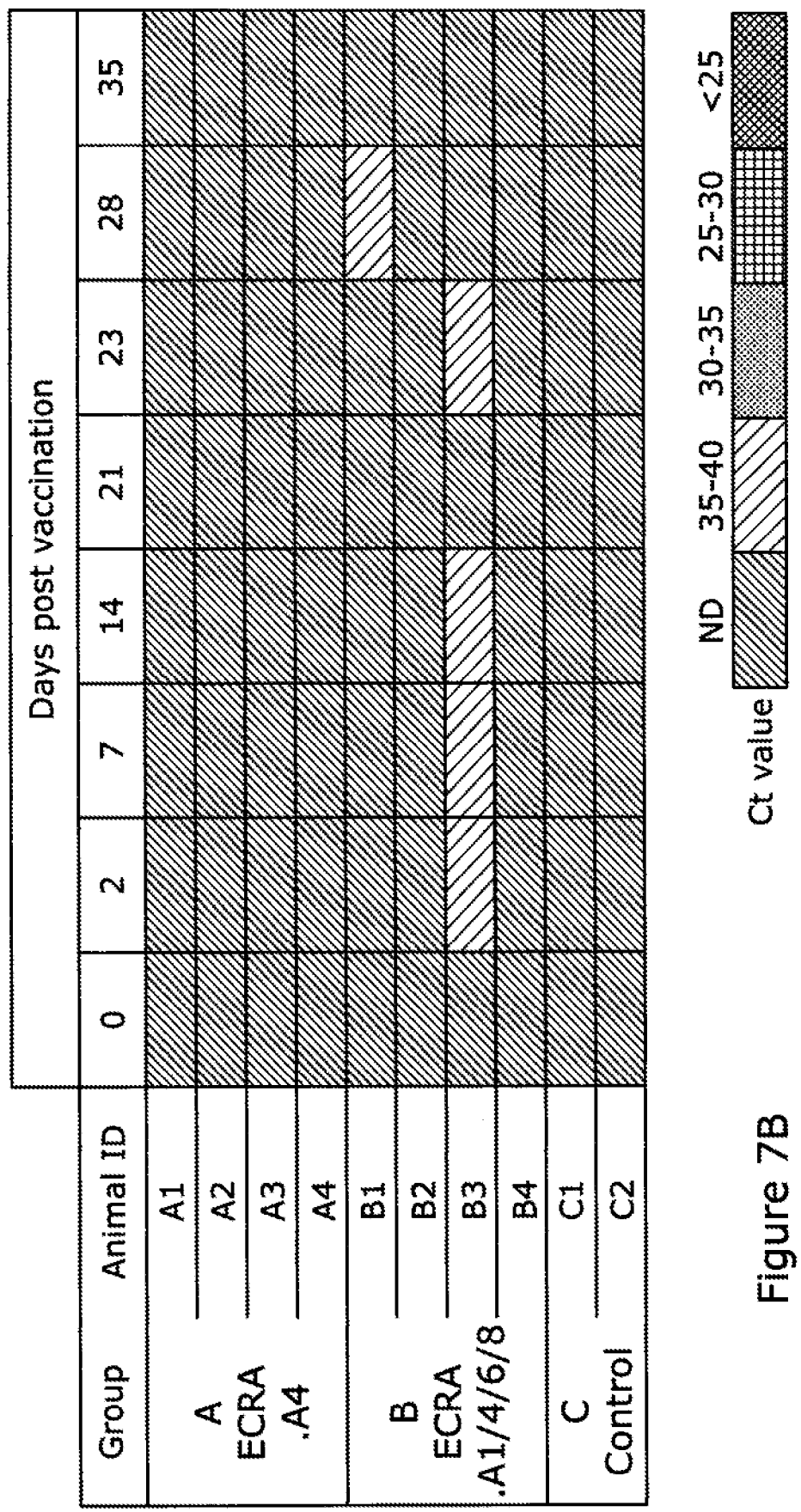

Vaccinated ponies were routinely monitored from day 0 to day 35 and as expected, none showed AHSV clinical reaction in contrast to the control animals (FIGS. 7A & B). Thus, the ECRA.AHSV vaccine strains induced no adverse effects in animals. Viral replication was also monitored by RT-PCR of the blood samples of the animals. As shown in FIG. 7B, from day 0 to day 35 viral RNA was either not detectable at all or present at a very low level in the vaccinated animals in both groups and were equivalent to the control animals. The data indicated the absence of viral replication after two doses of vaccinations.

Development of antibody response of ECRA.AHSV strains in ponies was initially monitored by a standard AHSV group specific VP7 antigen ELISA test. Even after the first dose of vaccination, vaccine elicited an immune response in the animals, which was further enhanced after a second vaccination (FIG. 8). As expected, the sera of the two control animals, C1 and C2, had no VP7 antibody, while all vaccinated animals of both groups A and B were seroconverted and high level of antibodies against VP7 which could be detected at day 28 and day 35, respectively 7 days and 14 days after the booster injection (FIG. 8).

The immune response was further analysed by determining the neutralization antibody titers of vaccinated animals versus control animals (Table 1). Neutralization against all serotypes included in the vaccine formulations were tested by plaque reduction assays at day 35 (prior to challenge). Serum samples collected at day 21 had very low, if any neutralizing antibody (NA) titers against any serotypes that could be detected (data not shown). However, sera collected at day 35 (two weeks after the booster vaccination) of all ECRA.A4 monovalent-vaccinated animals had NA titers (16-64) against AHSV4 (Table 1). All animals in group B, vaccinated with the cocktail vaccine, had NAs against all 4 serotypes, that were present in the vaccine cocktail. Most had strong NA titers (16-64) while some ponies developed NA titers as high as 128 against some serotypes (e.g., AHSV6 & 8) (Table 1).

Thus, newly developed vaccines are non-replicative in the vaccinated host and can generate an efficient neutralizing antibody response. Furthermore, the cocktail vaccination allowed production of neutralizing antibodies against all four serotypes.

Neutralizing Antibody Production and Clinical Protection after Challenge

To determine protective efficacy of the vaccines, two weeks after the booster vaccination, control and vaccinated animals were challenged only with $2 \times 10^6$ TCID$_{50}$ of virulent AHSV4, since it is considered to be the most pathogenic. Immune responses and clinical signs of each animal were monitored. High titers of neutralizing antibodies against AHSV4 were detected by SN assays at day 44 (8 days post challenge) in both group A and group B animals and up to 256 for 3 ponies (Table 2). Neutralizing antibody titers up to 32 were also detected against AHSV6 in 2 ponies and AHSV8 in 3 ponies of the group B. Twenty-four days after challenge (day 60) high titers of neutralizing antibodies against AHSV4 were still detectable in all animal of both groups, presumably due to the memory response triggered by the challenge virus. The B group ponies that elicited neutralizing antibodies against AHSV6 and AHSV8 also sustained neutralizing antibody production at day 60 (Table 2), indicating the strong immune response of the vaccine strains in natural hosts, either when used individually or in a mixture.

Figure 9A:
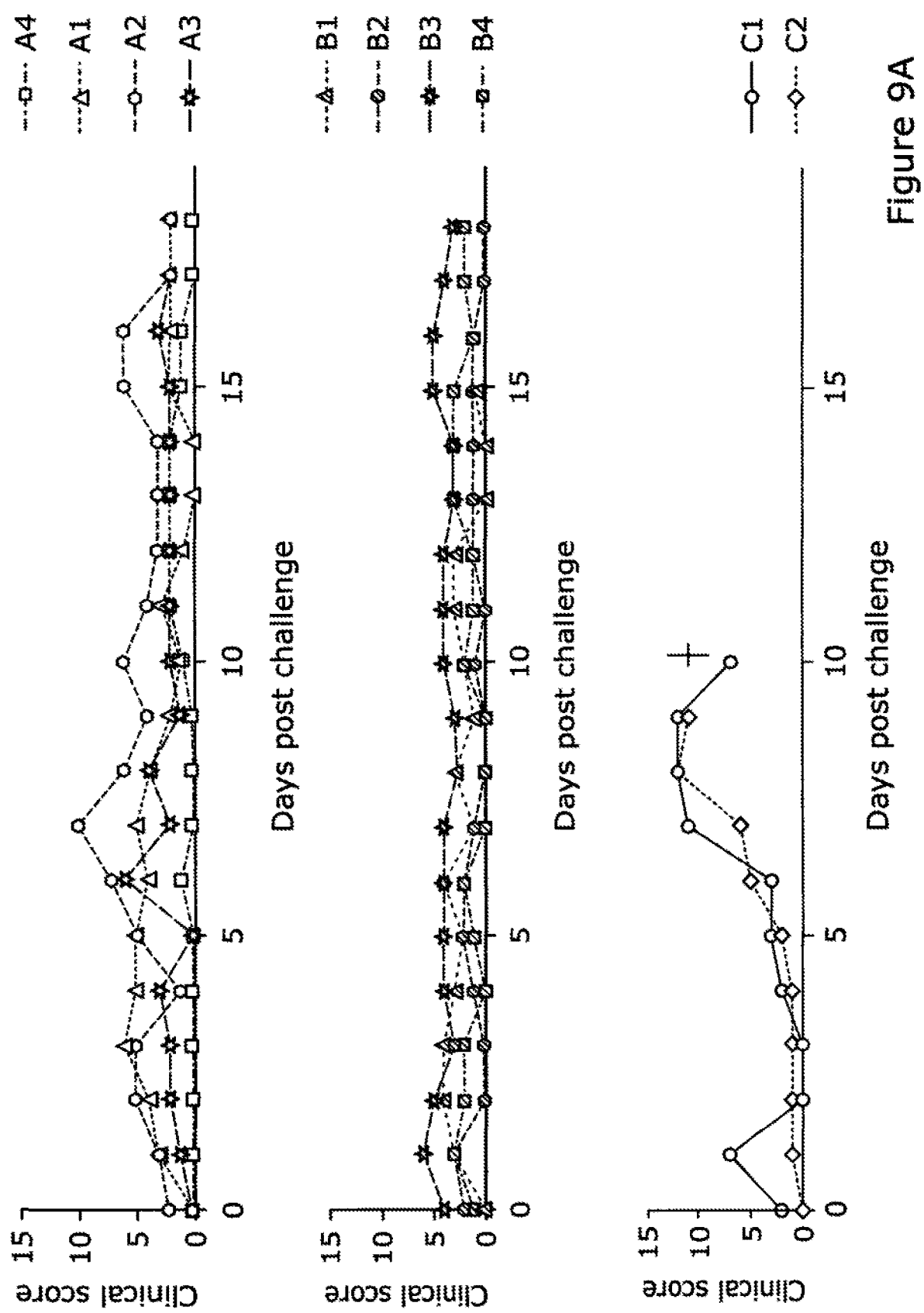

No neutralizing antibodies were detectable in control animals C1 and C2 (Table 2). As expected both control animals started to show clinical signs shortly (6 to 7 days) after challenge with virulent virus with apathy, high hyperthermia and respiratory distress, oedema of the eyelids and supraorbital fossae as well as nasal discharge. These animals were euthanized at 10 days (C2) and 11 days (C1) post challenge respectively (FIG. 9B). Necropsy performed on both control animals highlighted marked pulmonary oedema and pericardial and pleural effusions, which are consistent with AHSV infection. In contrast, vaccinated animals from group A and B showed no clinical signs (FIG. 9A top and middle panel respectively). Only one vaccinated animal, A2, showed mild circulatory (oedema of the eyelids, nasal discharge and moderate dyspnoea) and respiratory symptoms for only two days (6 to 8 days' post challenge) (FIG. 9A, top panel). This was probably due to lower neutralizing antibody titers (Table 2).

Figure 10:
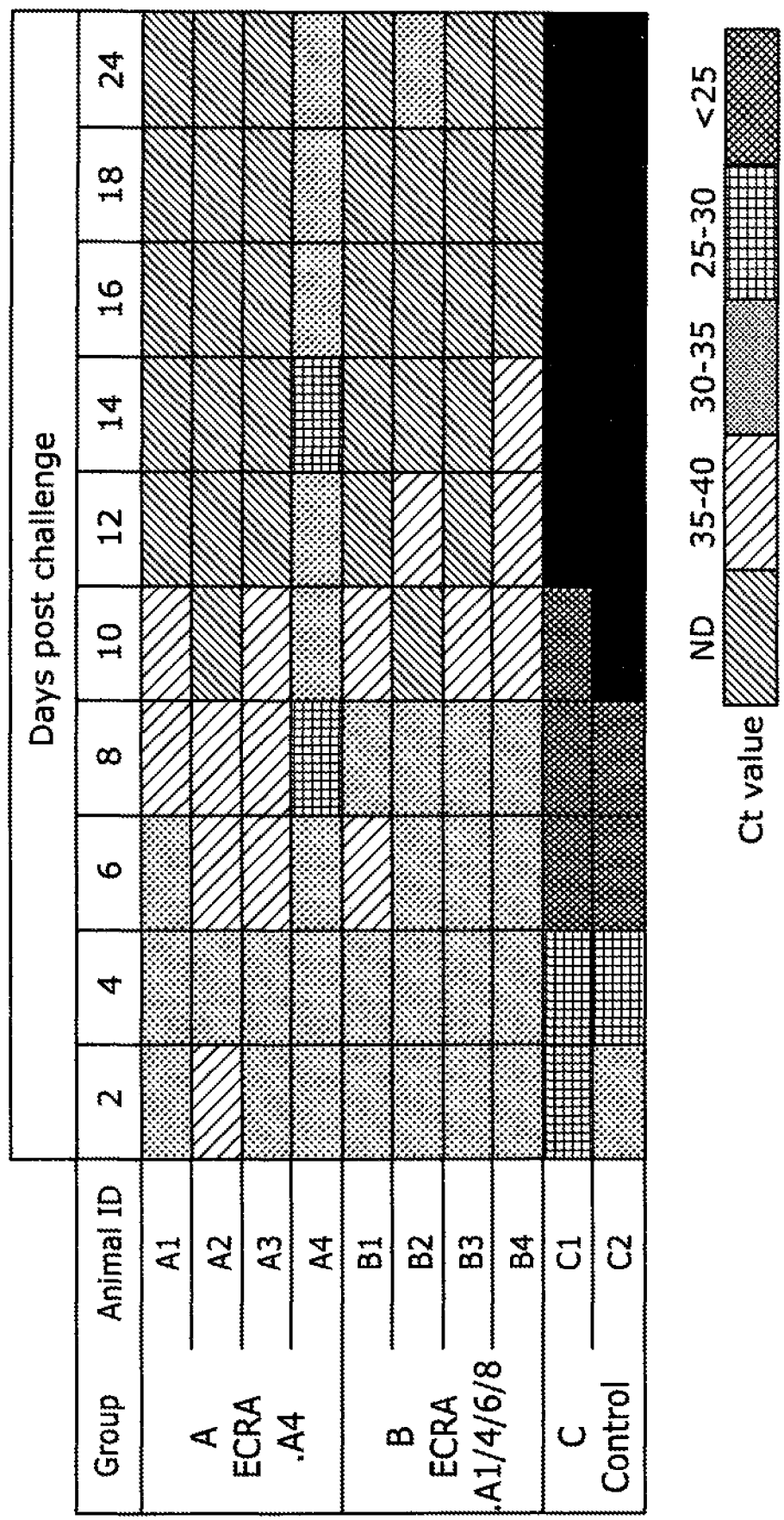
FIG. 10. Absence of virus replication in vaccinated animals. Viremia in blood samples was determined by RT-PCR. Ct values are represented with a colour gradient from green (high) to red (low) corresponding to low to high viral loads. Values above 40 were considered as not detected (ND). Control animals in group C (C1 and C2) were respectively euthanized at 11 and 10 days post challenge, due to severe AHS symptoms (black)

Viral replication was monitored in post challenged blood samples by RT-PCR. Both animals of the control group showed high viral loads (Ct of 26.9 and 27.1) 4 days after challenge and increased until 8 days after challenge (Ct of 17.5 and 15.6) (FIG. 10). These data were consistent with the severe symptoms observed during clinical monitoring (FIG. 9A, bottom panel, and 9B). RT-PCR analysis of post mortem animals detected the presence of AHSV4 RNA in the hearts, spleens and livers of C1 and C2 ponies (Ct from 14.85 to 20.37, data not shown). On the contrary, all vaccinated animals of group A and group B showed very low levels of AHSV4 from 2 to 8 days after challenge with virulent virus strain (Ct from 31.4 to 37.2). For certain animals, A4, B2 and B4, viral RNA could be detected in blood samples twelve days after the challenge (Ct from 30.1 to 38.1, FIG. 10), but no CPE was observed even after 4 passages in Vero cells (data not shown). Since B4 animal was pregnant, this could have explained the presence of viral RNA in her blood for a longer period when compared to the others (Ct up to 36, FIG. 10). However, the foal showed no viral RNA that could be detected by RT-PCR. The foal was born on day 59 after first vaccination and presumably after 345 days (±7 days) gestation period. It is noteworthy that virulent virus challenge was performed on 322 days of gestation (day 36 after first vaccination) and the first and second vaccine doses were inoculated on 286 days and 307 days respectively, of gestation. The new born foal had AHSV maternal antibodies detected at day 60 post prime vaccination and was completely normal and healthy without any sign of AHS disease. The data indicated that the challenged virulent virus did not cross the placenta. Fourteen days after challenge, the AHSV4 RNA was detected in one (A4) of four animals in group A (FIG. 10). But there were no clinical symptoms (FIG. 9A, top panel). Further, the serum of A4 pony had an increased level of neutralizing antibody titers against AHSV4, from 64 at day 44 (8 days after challenge) up to 256 at day 60 (24 days after challenge) (Table 2).

Taken altogether, these data demonstrate the safety of both ECRA.A4 and ECRA.A1/4/6/8 vaccination and the clinical protection afforded to vaccinated animals against a virulent AHSV4.

SUMMARY

African horse sickness virus (AHSV) expresses four major structural proteins: outer shell proteins VP2 and VP5, middle core VP7 and sub-core VP3. To generate an efficient reverse genetics (RG) system with which to study the roles of these proteins in virus particle formation, we developed a cell line expressing a heterologous VP6 for complementation of VP6-deficient virus in trans. The ORF of the essential replicative enzyme VP6, as well as the overlapping ORF of a lesser studied NS4 protein, in segment 9 of AHSV were disrupted by introducing multiple stop-codons.

Through the introduction of 11 stop codons (TAA or TGA) throughout the S9 gene we disrupted the ORFs of VP6 and NS4, but retained the length of the obtained S9multistop, advantageously, minimizing the genetic pressure on the defective AHSV rescue and replication.

In parallel, a cell line expressing AHSV VP6 was established to provide complementation of a functional gene product during rescue of multistop disabled virus. Finally, after confirming a propagation-deficient phenotype for a disabled virus platform, viral RNA segments encoding different serotype-determining capsid proteins were exchanged to obtain serotypes or chimeras that would cover the greater part of the antigenic space of AHSV.

Therefore, complementation (of lacking protein) represents a safe AHSV vaccine platform with minimized genetic pressure towards restoring viral virulence. Notably, by introducing multiple stop codons to disrupt the ORFs of AHSV segment 9 (e.g. coding for VP6 and NS4) passaging in a complementary cell line did not reveal changes in the mutated S9, which would restore any of mutated ORFs.

Also, our results have demonstrated that all 9 ASHV disabled viruses were able to replicate in a complementary cell line at titers close to wt AHSV. At the same time, all defective viruses were disabled in other tested cell lines of mammalian and insect origin.

Therefore our approach and the generated isolated ssRNA/vaccinal strains produced provide superior, safe and efficient AHSV vaccines. Indeed, we evaluated the protective efficacies of these defective viruses in AHSV natural hosts, e.g. ponies. One monoserotype (ECRA.A4) vaccine and one multivalent cocktail (ECRA.A1/4/6/8) vaccine were tested and ponies were challenged with a virulent AHSV4. All vaccinated ponies were protected and did not develop severe clinical symptoms of AHS. Furthermore, the multivalent cocktail vaccinated ponies produced neutralizing antibodies against all serotypes present in the cocktail, and a foal born during the trial was healthy and had no viremia. These results validate the suitability of these ECRA strains as a new generation of vaccines for AHSV.

REFERENCES

17. Boyce M, Celma C C, Roy P. 2008. Development of reverse genetics systems for bluetongue virus: recovery of infectious virus from synthetic RNA transcripts. J Virol 82:8339-8348.
18. Matsuo E, Roy P. 2009. Bluetongue virus VP6 acts early in the replication cycle and can form the basis of chimeric virus formation. J Virol 83:8842-8848.
23. Kaname Y, Celma C C, Kanai Y, Roy P. 2013. Recovery of African horse sickness virus from synthetic RNA. J Gen Virol 94:2259-2265.
24. Wechsler S J, McHolland L E, Tabachnick W J. 1989. Cell lines from *Culicoides variipennis* (Diptera: Ceratopogonidae) support replication of bluetongue virus. J Invertebr Pathol 54:385-393.
25. Quan M, Lourens C W, MacLachlan N J, Gardner I A, Guthrie A J. 2010. Development and optimisation of a duplex real-time reverse transcription quantitative PCR assay targeting the VP7 and NS2 genes of African horse sickness virus. J Virol Methods 167:45-52.
26. Toussaint J F, Sailleau C, Breard E, Zientara S, De Clercq K. 2007. Bluetongue virus detection by two real-time RT-qPCRs targeting two different genomic segments. J Virol Methods 140:115-123.

TABLE 1

| Group | Animal ID | Neutralizing antibody titers Day 35 of vaccination | | | |
|---|---|---|---|---|---|
| | | AHSV 1 | AHSV 4 | AHSV 6 | AHSV 8 |
| A | A1 | nd | 16 | nd | nd |
| ECRA.A4 | A2 | nd | 32 | nd | nd |
| | A3 | nd | 64 | nd | nd |
| | A4 | nd | 32 | nd | nd |
| B | B1 | 64 | 16 | 32 | 32 |
| ECRA.A1/ | B2 | 16 | 16 | 8 | 32 |
| 4/6/8 | B3 | 64 | 32 | 128 | 128 |
| | B4 | 16 | 8 | 16 | 64 |
| C | C1 | — | — | — | — |
| Control | C2 | — | — | — | — |

TABLE 2

| Group | Animal ID | Neutralizing antibody titers | | | | | | | | | |
|---|---|---|---|---|---|---|---|---|---|---|---|
| | | Day 44 of vaccination | | | | | Day 60 of vaccination | | | | |
| | | AHSV 1 | AHSV 4 | AHSV 5 | AHSV 6 | AHSV 8 | AHSV 1 | AHSV 4 | AHSV 5 | AHSV 6 | AHSV 8 |
| A | A1 | nd | 64 | nd | nd | nd | nd | 32 | nd | nd | nd |
| ECRA.A4 | A2 | nd | 32 | nd | nd | nd | nd | 16 | nd | nd | nd |
| | A3 | nd | ≥256 | nd | nd | nd | nd | 64 | nd | nd | nd |
| | A4 | nd | 64 | nd | nd | nd | nd | ≥256 | nd | nd | nd |
| B | B1 | — | 32 | — | 4 | 8 | — | 16 | — | 4 | 8 |
| ECRA.A1/4/6/8 | B2 | — | 64 | — | — | 8/16 | — | 32 | — | — | 4 |
| | B3 | 4 | ≥256 | 4 | 16 | 32 | 4 | 128 | — | 16 | 32 |
| | B4 | — | ≥256 | 4 | — | 8 | — | 32 | — | — | — |
| C | C1 | — | 4 | — | — | — | nd | nd | nd | nd | nd |
| Control | C2 | — | — | — | — | — | nd | nd | nd | nd | nd |

The invention claimed is:

1. An isolated viral ssRNA comprising at least a part of an S9 segment from an African Horse Sickness Virus (AHSV) genome, wherein the at least a part of the S9 segment comprises a plurality of mutations, each mutation providing or encoding a stop codon that destroys a function of at least one essential gene while retaining a length of the S9 segment.

2. The isolated viral ssRNA according to claim 1, wherein said at least one essential gene is selected from the group consisting of VP6 and NS4.

3. The isolated viral ssRNA according to claim 1, wherein said plurality of mutations destroy the function of at least VP6 and NS4.

4. The isolated viral ssRNA according to claim 1, wherein said plurality of mutations are introduced at or between nucleotides 288-877 of the S9 segment.

5. The isolated viral ssRNA according to claim 1, wherein said plurality of mutations are introduced at or between one or more of the following nucleotide sites: nucleotides 288-304; nucleotides 377-386; nucleotides 590-608; and nucleotides 872-877 of the S9 segment.

6. The isolated viral ssRNA according to claim 5, wherein at least one mutation is introduced into each of the nucleotide sites.

7. The isolated viral ssRNA according to claim 5, wherein at least the following mutations are introduced:
   a. at least 3 mutations at or between nucleotides 288-304 of the S9 segment;
   b. at least 3 mutations at or between nucleotides 377-386 of the S9 segment;
   c. at least 3 mutations at or between nucleotides 590-608 of the S9 segment; and
   d. at least 2 mutations at or between nucleotides 872-877 of the S9 segment.

8. The isolated viral ssRNA according to claim 7, wherein a further frameshift mutation is introduced at or between nucleotides 288-304 of the S9 segment which encodes a stop codon that destroys the function of NS4.

9. A cell infected with the isolated viral ssRNA of claim 1, wherein the cell expresses at least one essential gene of the S9 segment of AHSV that complements said at least one essential gene mutated in the ssRNA, which thereby enables the replication of a vaccinal viral strain in the cell.

10. A vaccinal viral strain comprising the isolated viral ssRNA according to claim 1.

11. The vaccinal viral strain according to claim 10, wherein the vaccinal viral strain is serotype specific and comprises AHSV1, AHSV2, AHSV3, AHSV4, AHSV5, AHSV6, AHSV7, AHSV8 or AHSV9.

12. The vaccinal viral strain according to claim 11, comprising any combination of AHSV1-9 or all of AHSV1-9.

13. A pharmaceutical composition comprising the vaccinal viral strain of claim 10 in combination with a pharmaceutically acceptable carrier, adjuvant or vehicle.

14. A pharmaceutical composition comprising the isolated viral ssRNA of claim 1 in combination with a pharmaceutically acceptable carrier, adjuvant or vehicle.

15. A combination therapeutic comprising a pharmaceutical composition according to claim 13 and one or more additional anti-viral agent(s).

16. A method for vaccinating a non-human animal against AHSV, the method comprising delivering or administering an effective amount of the vaccinal viral strain according to claim 10 to a non-human animal.

17. A method for vaccinating a non-human animal against AHSV, the method comprising delivering or administering an effective amount of the isolated viral ssRNA according to claim 1 to a non-human animal.

18. The method of claim 16, wherein said non-human animal is a horse, pony, mule, donkey, or zebra.

19. A kit comprising:
   an isolated viral ssRNA comprising at least a part of an S9 segment from an African Horse Sickness Virus (AHSV) genome, wherein the at least a part of the S9 segment comprises a plurality of mutations, each mutation providing or encoding a stop codon that destroys a function of at least one essential gene while retaining a length of the S9 segment; and a cell expressing at least one essential gene of the at least a part of S9 segment from AHSV that complements said at least one essential gene mutated in the ssRNA, which thereby enables replication of a vaccinal viral strain in the cell.

20. A method for generating defective AHSV virus of a given serotype, comprising:
    a) introducing a plurality of mutations in an S9 segment of said virus while retaining a length of the S9 segment, each mutation providing or encoding a stop codon that destroys a function of at least one essential gene; and
    b) reassorting or exchanging the following selected segments S2+S6; S2+S6+S7; S2+S6+S7+S3; or S2+S6+S7+S3+S10 to generate the following serotypes def-AHSV8 and def-AHSV9 serotypes; def-AHSV3 and def-AHSV4; def-AHSV5, def-AHSV6 and def-AHSV7; and def-AHSV2 respectively.

21. A method for generating defective AHSV virus of a given serotype, comprising:
    a) introducing a plurality of mutations in an S9 segment of said virus while retaining a length of the S9 segment, each mutation providing or encoding a stop codon; and
    b) reassorting or exchanging the following selected segments to generate the following serotypes:
    the reassortment of two segments (S2+S6) encoding outer shell proteins VP2 and VP5 to generate def-AHSV8 and def-AHSV9 serotypes; and/or
    the reassortment of the two segments (S2+S6) encoding outer shell proteins VP2 and VP5 and the segment (S7) encoding middle-core protein VP7 to generate def-AHSV3 and def-AHSV4; and/or
    the reassortment of the two segments (S2+S6) encoding outer shell proteins VP2 and VP5 and the segment (S7) encoding middle-core protein VP7 and the segment (S3) encoding middle-core protein VP3 to generate def-AHSV5, def-AHSV6 and def-AHSV7; and/or
    the reassortment of the two segments (S2+S6) encoding outer shell proteins VP2 and VP5 and the segment (S7) encoding middle-core protein VP7 and the segment (S3) encoding middle-core protein VP3 and the segment (S10) encoding NS3/NS3A to generate def-AHSV2.

22. A combination therapeutic comprising the pharmaceutical composition according to claim 14 and one or more additional anti-viral agent(s).

23. The method of claim 17, wherein said non-human animal is a horse, pony, mule, donkey, or zebra.

* * * * *